(12) United States Patent
Beck et al.

(10) Patent No.: US 6,579,885 B2
(45) Date of Patent: Jun. 17, 2003

(54) ARYL AND HETEROARYL SUBSTITUTED TETRAHYDROISOQUINOLINES AND USE THEREOF

(75) Inventors: James P. Beck, Kalamazoo, MI (US); Matt A. Curry, Coatesville, PA (US); Mark A. Smith, Landenberg, PA (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 10/091,949

(22) Filed: Mar. 6, 2002

(65) Prior Publication Data

US 2002/0143014 A1 Oct. 3, 2002

Related U.S. Application Data

(63) Continuation of application No. 09/704,305, filed on Nov. 2, 2000.
(60) Provisional application No. 60/163,269, filed on Nov. 3, 1999.

(51) Int. Cl.$^7$ .................. C07D 217/02; C07D 401/06; A61K 31/4725; A61K 31/472
(52) U.S. Cl. ................ 514/307; 514/309; 514/310; 514/256; 514/241; 514/308; 514/266; 514/253; 514/233.5; 514/232.5; 514/228.2; 514/259; 456/140; 456/141; 456/142; 456/144; 456/148; 544/333; 544/180; 544/284; 544/363; 544/264; 544/357; 544/128; 544/80; 544/62
(58) Field of Search .................. 546/141, 142, 546/144, 140, 148; 544/333, 264, 80; 514/256, 308, 259, 233.5

(56) References Cited

U.S. PATENT DOCUMENTS

| | | | |
|---|---|---|---|
| 3,666,763 A | 5/1972 | Grethe et al. | |
| 3,947,456 A | 3/1976 | Rheiner | |
| 4,843,071 A | 6/1989 | Hohenwarter | |
| 4,902,710 A | 2/1990 | Foster et al. | |
| 5,444,070 A | 8/1995 | Moldt et al. | |
| 5,532,244 A | 7/1996 | Wong et al. | |
| 5,654,296 A | 8/1997 | Kato et al. | |
| 5,789,449 A | 8/1998 | Norden | |
| 6,121,261 A | 9/2000 | Glatt et al. | |
| 6,136,803 A | 10/2000 | Freedman et al. | |

FOREIGN PATENT DOCUMENTS

| | | |
|---|---|---|
| CA | 2015114 | 10/1990 |
| CH | 538 477 | 8/1973 |
| DE | 2 062 001 | 7/1971 |
| EP | 0 360 390 A1 | 3/1990 |
| EP | 0 400 319 A1 | 4/1990 |
| EP | 0 394 989 B1 | 10/1990 |
| EP | 0 428 434 A2 | 5/1991 |
| EP | 0 429 366 B1 | 5/1991 |
| EP | 0 430 771 B1 | 6/1991 |
| EP | 0 436 334 B1 | 7/1991 |
| EP | 0 443 132 B1 | 8/1991 |
| EP | 0 482 539 B1 | 4/1992 |
| EP | 0 498 069 B1 | 8/1992 |
| EP | 0 499 313 B1 | 8/1992 |
| EP | 0 512 901 B1 | 11/1992 |
| EP | 0 512 902 A1 | 11/1992 |
| EP | 0 514 273 A1 | 11/1992 |
| EP | 0 514 274 A1 | 11/1992 |
| EP | 0 514 275 A1 | 11/1992 |
| EP | 0 514 276 A1 | 11/1992 |
| EP | 0 515 681 A1 | 12/1992 |
| EP | 0 520 555 A1 | 12/1992 |
| EP | 0 522 808 A2 | 1/1993 |
| EP | 0 528 495 A1 | 2/1993 |
| EP | 0 533 280 B1 | 3/1993 |

(List continued on next page.)

OTHER PUBLICATIONS

Cliffe et al., "(S)–N–tert–Butyl–3–(4–(2–methoxyphenyl)–piperazin – 1–yl)–2–phenylpropanamide [(S)–WAY–100135]: A Selective Antagonist at Presynaptic and Postsynaptic–5–HT$_{1A}$ Receptors" *J. Med. Chem.* 36:1509–10 (1993).

Salama et al., "Antigenic Determinants Responsible for the Reactions of Drug–Dependent Antibodies with Blood Cells," *British Journal of Haematology* 78:535–539 (1991).

Trepanier et al., "3,4–Dihydroisocarbostyril and 1,2,3, 4–Tetrahydroisoquinoline Derivatives of Ephedrine," *Journal fo Medicinal Chemistry* 16(4):342–347 (1973).

Miller et al., "An Efficient Synthesis of 4–Aryl–1,2,3,4–Tetrahydroisoquinolines," *Synthetic Communications* 24(8):1187–1193 (1994).

(List continued on next page.)

*Primary Examiner*—John M. Ford
(74) *Attorney, Agent, or Firm*—Nixon Peabody LLP

(57) ABSTRACT

Provided herein are compounds of the formula (I):

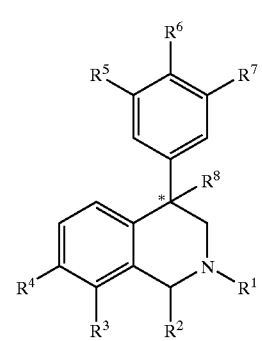

(I)

wherein $R^1$–$R^8$ are as described herein, $R^4$ being aryl or heteroaryl Such compounds are particularly useful in the treatment of a disorder which is created by or is dependent upon decreased availability of serotonin, norepinephrine or dopamine.

25 Claims, No Drawings

FOREIGN PATENT DOCUMENTS

| | | |
|---|---|---|
| EP | 0 536 817 A1 | 4/1993 |
| EP | 0 545 478 A1 | 6/1993 |
| EP | 0 558 156 A2 | 9/1993 |
| EP | 0 577 394 B1 | 1/1994 |
| EP | 0 585 913 B1 | 3/1994 |
| EP | 0 599 338 A2 | 6/1994 |
| EP | 0 599 538 A1 | 6/1994 |
| EP | 0 610 793 A1 | 8/1994 |
| EP | 0 708 101 B1 | 10/1994 |
| EP | 0 634 402 A1 | 1/1995 |
| EP | 0 532 456 B1 | 3/1995 |
| EP | 0 707 006 B1 | 10/1995 |
| EP | 0 686 629 A2 | 12/1995 |
| EP | 0 693 489 A1 | 1/1996 |
| EP | 0 694 535 A1 | 1/1996 |
| EP | 0 699 674 A1 | 3/1996 |
| EP | 0 709 375 A2 | 5/1996 |
| EP | 0 709 376 A2 | 5/1996 |
| EP | 0 714 891 A1 | 6/1996 |
| EP | 0 723 959 A1 | 7/1996 |
| EP | 0 733 632 A1 | 9/1996 |
| EP | 0 517 589 B1 | 12/1996 |
| EP | 0 776 893 A1 | 6/1997 |
| EP | 0 699 655 B1 | 9/1997 |
| EP | 0 520 555 B1 | 9/1999 |
| GB | 2 266 529 A | 11/1993 |
| GB | 2 268 931 A | 1/1994 |
| GB | 2 269 170 A | 2/1994 |
| GB | 2 269 590 A | 2/1994 |
| GB | 2 271 566 A | 4/1994 |
| GB | 2 271 774 A | 4/1994 |
| GB | 2 292 144 A | 2/1996 |
| GB | 2 293 168 A | 3/1996 |
| GB | 2 293 169 A | 3/1996 |
| GB | 2 302 689 A | 1/1997 |
| JP | 04193867 | 7/1992 |
| WO | WO 90/05525 | 5/1990 |
| WO | WO 90/05729 | 5/1990 |
| WO | WO 91/09844 | 7/1991 |
| WO | WO 91/18899 | 12/1991 |
| WO | WO 92/01688 | 2/1992 |
| WO | WO 92/06079 | 4/1992 |
| WO | WO 92/12151 | 7/1992 |
| WO | WO 92/15585 | 9/1992 |
| WO | WO 92/17449 | 10/1992 |
| WO | WO 92/20661 | 11/1992 |
| WO | WO 92/20676 | 11/1992 |
| WO | WO 92/21677 | 12/1992 |
| WO | WO 92/22569 | 12/1992 |
| WO | WO 93/00330 | 1/1993 |
| WO | WO 93/00331 | 1/1993 |
| WO | WO 93/01159 | 1/1993 |
| WO | WO 93/01165 | 1/1993 |
| WO | WO 93/01169 | 1/1993 |
| WO | WO 93/01170 | 1/1993 |
| WO | WO 93/06099 | 4/1993 |
| WO | WO 93/09116 | 5/1993 |
| WO | WO 93/10073 | 5/1993 |
| WO | WO 93/14084 | 7/1993 |
| WO | WO 93/14113 | 7/1993 |
| WO | WO 93/18023 | 9/1993 |
| WO | WO 93/19064 | 9/1993 |
| WO | WO 93/21155 | 10/1993 |
| WO | WO 93/21181 | 10/1993 |
| WO | WO 93/23380 | 11/1993 |
| WO | WO 93/24465 | 12/1993 |
| WO | WO 94/00440 | 1/1994 |
| WO | WO 94/01402 | 1/1994 |
| WO | WO 94/02461 | 2/1994 |
| WO | WO 94/02595 | 2/1994 |
| WO | WO 94/03429 | 2/1994 |
| WO | WO 94/03445 | 2/1994 |
| WO | WO 94/04494 | 3/1994 |
| WO | WO 94/04496 | 3/1994 |
| WO | WO 94/05625 | 3/1994 |
| WO | WO 94/07843 | 4/1994 |
| WO | WO 94/08997 | 4/1994 |
| WO | WO 94/10165 | 5/1994 |
| WO | WO 94/10167 | 5/1994 |
| WO | WO 94/10168 | 5/1994 |
| WO | WO 94/10170 | 5/1994 |
| WO | WO 94/11368 | 5/1994 |
| WO | WO 94/13639 | 6/1994 |
| WO | WO 94/13663 | 6/1994 |
| WO | WO 94/14767 | 7/1994 |
| WO | WO 94/15903 | 7/1994 |
| WO | WO 94/19320 | 9/1994 |
| WO | WO 94/19323 | 9/1994 |
| WO | WO 94/20500 | 9/1994 |
| WO | WO 94/26735 | 11/1994 |
| WO | WO 94/26740 | 11/1994 |
| WO | WO 94/29309 | 12/1994 |
| WO | WO 95/02595 | 1/1995 |
| WO | WO 95/04040 | 2/1995 |
| WO | WO 95/04042 | 2/1995 |
| WO | WO 95/06645 | 3/1995 |
| WO | WO 95/07886 | 3/1995 |
| WO | WO 95/07908 | 3/1995 |
| WO | WO 95/08549 | 3/1995 |
| WO | WO 95/11880 | 5/1995 |
| WO | WO 95/14017 | 5/1995 |
| WO | WO 95/15311 | 6/1995 |
| WO | WO 95/16679 | 6/1995 |
| WO | WO 95/17382 | 6/1995 |
| WO | WO 95/18124 | 7/1995 |
| WO | WO 95/18129 | 7/1995 |
| WO | WO 95/20575 | 8/1995 |
| WO | WO 95/21819 | 8/1995 |
| WO | WO 95/22525 | 8/1995 |
| WO | WO 95/23798 | 9/1995 |
| WO | WO 95/26338 | 10/1995 |
| WO | WO 95/28418 | 10/1995 |
| WO | WO 95/30674 | 11/1995 |
| WO | WO 95/30687 | 11/1995 |
| WO | WO 95/33744 | 12/1995 |
| WO | WO 96/05181 | 2/1996 |
| WO | WO 96/05193 | 2/1996 |
| WO | WO 96/05203 | 2/1996 |
| WO | WO 96/06094 | 2/1996 |
| WO | WO 96/07649 | 3/1996 |
| WO | WO 96/10562 | 4/1996 |
| WO | WO 96/16939 | 6/1996 |
| WO | WO 96/18643 | 6/1996 |
| WO | WO 96/20197 | 7/1996 |
| WO | WO 96/21661 | 7/1996 |
| WO | WO 96/29304 | 9/1996 |
| WO | WO 96/29317 | 9/1996 |
| WO | WO 96/29326 | 9/1996 |
| WO | WO 96/29328 | 9/1996 |
| WO | WO 96/31214 | 10/1996 |
| WO | WO 96/32385 | 10/1996 |
| WO | WO 96/37489 | 11/1996 |
| WO | WO 97/01553 | 1/1997 |
| WO | WO 97/01554 | 1/1997 |
| WO | WO 97/03066 | 1/1997 |
| WO | WO 97/08144 | 3/1997 |
| WO | WO 97/14671 | 4/1997 |
| WO | WO 97/17362 | 5/1997 |
| WO | WO 97/18206 | 5/1997 |
| WO | WO 97/19084 | 5/1997 |
| WO | WO 97/19942 | 6/1997 |

| WO | WO 97/21702 | 6/1997 |
| WO | WO 97/23458 | 7/1997 |
| WO | WO 97/36876 | 10/1997 |
| WO | WO 97/49710 | 12/1997 |
| WO | WO 98/40358 | 9/1998 |

OTHER PUBLICATIONS

Tirelli et al., "Differential Effects of Direct and Indirect Dopamine Agonists on the Induction of Gnawing in C57Bl/6J Mice," *Journal of Pharmacology and Experimental Therapeutics* 273(1):7–15 (1995).

Jacob et al., "Dopamine Agonist Properties of N–Alkyl–4–(3,4–dihydroxyphenyl)–1,2,3,4–tetrahydroisoquinolines," *J. Med. Chem.* 24:1013–1015 (1981).

Ishikura et al., "The Synthesis of 4–Substituted Isoquinoline Derivatives from Diethyl (4–Isoquinolyl) Borane," *Heterocycles*, 26:1603–1610 (1987).

Mondeshka et al., "Synthesis, Antiulcer and Antidepressive Activity of 4–(4–Halophenyl)–2–Phenyl–1,2,3,4–Tetrahydroisoquinolines," *IL Farmaco* 49:475–480 (1994).

Berge et al., "Pharmaceutical Salts," *Journal of Pharmaceutical Sciences* 66(1):1–19 (1977).

Bundgaard, *Design of Prodrugs*, Amsterdam, The Netherlands: Elsevier Science Publishers B.V. (1985) (Table of Contents only).

Krogsgaard–Larsen et al., eds., *A Textbook of Drug Design and Development*, Chur, Switzerland: Harwood Academic Publishers GmbH (1991) (Table of Contents only).

Bundgaard, "Means to Enhance Penetration," *Advanced Drug Delivery Reviews* 8:1–38 (1992).

Nielsen et al., "Glycolamide Esters as Biolabile Prodrugs of Carboxylic Acid Agents: Synthesis, Stability, Bioconversion, and Physicochemical Properties," *Journal of Pharmaceutical Sciences* 77(4):285–298 (1988).

Kakeya et al., "Studies on Prodrugs of Cephalosporins. I. Synthesis and Biological Properties of Glycyloxybenzoyloxymethyl and Glycylaminobenzoyloxymethyl Esters of 7β–[2–(2–Aminothiazol–4–yl)–(Z)–2–Methoxyiminoacetamido]–3–Methyl–3–Cephem–4–Carboxylic Acid" *Chem. Pharm. Bull.* 32(2):692–698 (1984).

Middlemiss et al., "Centrally Active 5–HT Receptor Agonists and Antagonists," *Neuroscience & Biobehavioral Reviews* 16:75–82 (1992).

Greene et al., *Protective Groups in Organic Synthesis*, 2d. Ed., New York, New York: John Wiley & Sons, Inc. (1991) (Table of Contents only).

McOmie, ed., *Protective Groups in Organic Chemistry*, London: Plenum Press (1973) (Table of Contents only).

Jorgenson, "Preparations of Ketones from the Reaction of Organolithium Reagents with Carboxylic Acids," Dauben et al., eds., *Organic Reactions*, vol. 18, New York, New York: John Wiley & Sons, Inc., pp. 1–97 (1970) (Table of Contents only).

Larock, *Comprehensive Organic Transformations: A Guide to Functional Group Preparation*, New York, New York: VCH Publishers, Inc. (1989) (Table of Contents only).

Venkov et al., "A New Synthesis of 1,2,3,4–Tetrahydro–2–Methyl–4–Phenylisoquinolines," *Synthesis* 253–255 (1990).

Dandridge et al., "Synthesis, Resolution, Absolute Stereochemistry, and Enantioselectivity of 3', 4'–Dihydroxynomifensine," *J. Med. Chem.* J. Med. Chem. 27:28–35 (1984).

Kihara, et al., "A Convenient Synthesis of 4–Substituted 1,2,3,4–Tetrahydroisoquinolin–4–OLS by a Novel Intramolecular Barbier Reaction and by an Insertion Reaction: Reaction Scope and Limitations." *Tetrahedron* 48(1): 67–78 (1992).

Hudlicky, "Fluorination with Diethylaminosulfur Trifluoride and Related Aminofluorosulfuranes," *Organic Reactions* 35:513–637 (1985).

Gao et al., "Asymmetric Hetero Diels–Alder Reaction Catalyzed by Stable and Easily Prepared CAB Catalysts," *Tetrahedron* 50(4):979–988 (1994).

Dudley et al., "The Actions of Xylamine on Central Noradrenergic Neurons," *The Journal of Pharmacology and Experimental Therapeutics* 217(3):834–840 (1981).

Stille, "Zur pharmakologischen Prufung von Antidepressiva am Beispiel eines Dibenzodiazepins," *Arzneimittel–Forschung* 14:534–537 (1964) (English summary included).

Blomberg et al., "The Barbier Reaction—A One Step Alternative for Synthesis via Organomagnesium Compounds," *Synthesis* pp. 18–30 (1977).

Maryanoff et al., "Pyrroloisoquinoline Antidepressants. 2. In–Depth Exploration of Structure–Activity Relationships," *J. Med. Chem.* 30(8):1433–1454 (1987).

Kihara et al., "Synthesis and Pharmacological Evaluation of Phenolic 2–Methyl–4–Phenyl–1,2,3,4,–Tetrahydroisoquinolin–4–ols As New Norepinephrine Potentiator," *Drug Design and Discovery* 11(3):175–183 (1994).

Kihara et al., "Synthesis and Enantioselectivity of Optically Active 1– and 3–Substituted 4–Phenyl–1,2,3,4–Tetrahydroisoquinolin–4–ols and Related Compounds As Norepinephrine Potentiators," *Chemical and Pharmaceutical Bulletin* 43(9):1543–1546 (1995).

ARYL AND HETEROARYL SUBSTITUTED TETRAHYDROISOQUINOLINES AND USE THEREOF

FIELD OF THE INVENTION

The present invention relates to compounds, compositions, methods for the treatment of various neurological and psychological disorders, and the use of the compounds in combination therapy. In particular, the present invention relates to such compounds, compositions and methods wherein the compounds are novel 4-phenyl substituted tetrahydroisoquinolines derivatives.

BACKGROUND OF THE INVENTION

Serotonin, dopamine and norepinephrine are known to be important chemical messengers participating in the transmission of nerve impulses in the brain. These messengers are liberated at specific sites on pre-synaptic cells and received, to complete transmission of the impulse, at specific sites on post-synaptic cells. Their effect is then terminated by metabolism or by uptake into the pre-synaptic cells. Drugs capable of blocking the pre-synaptosomal uptake of either of these chemical messengers in the brain, are useful in alleviating disorders associated with decreased levels of these chemical messengers. For example, duloxetine and fluoxetine which are known serotonin reuptake inhibitors have been found to be useful in the treatment of depression, obesity and obsessive-compulsive disease (Wong, et al., U.S. Pat. No. 5,532,244). Also, Moldt, et al., U.S. Pat. No. 5,444,070, discloses the use of dopamine reuptake inhibitors in the treatment of depression, Parkinsonism, drug addiction and/or abuse, cocaine and/or amphetamine addiction and/or abuse. Freedman, et al., U.S. Pat. No. 6,136,803 also discloses synaptic norepinephrine or serotonin uptake inhibitors which are useful in treating depression in a patient. Furthermore, Norden, U.S. Pat. No. 5,789,449 discloses the use of serotonin re-uptake inhibitors in treating psychiatric symptoms consisting of anger, rejection sensitivity, and lack of mental or physical energy. Also, Foster, et al., U.S. Pat. No. 4,902,710, discloses the use of serotonin and norepinephrine uptake inhibitors in suppressing the desire of humans to smoke or consume alcohol. Thus, there continues to remain a need to develop novel compounds which block reuptake of norephinephrine, dopamine or serotonin.

Compounds which inhibit the reuptake of serotonin or norepinephrine, have also been used in combination therapy. For example, Glatt, et al., U.S. Pat. No. 6,121,261 discloses the use of selective serotonin reuptake Inhibitors or norephinephrine uptake inhibitiors, in combination with neurokinin-1 receptor antagonist for treating attention deficit disorder in a patient.

Also, Hohenwarter, U.S. Pat. No. 4,843,071 discloses the use of a norepinephrine re-uptake inhibitor and a norepinephrine precursor in the treatment of obesity, drug abuse, or narcolepsy in a patient. Furthermore, Wong, et al., U.S. Pat. No. 5,532,244, discloses the use of serotonin reuptake inhibitors in combination with a serotonin 1A receptor antagonist, to increase the availability of serotonin, norepinephrine and dopamine in the brain.

The treatment of a variety of neurological and psychiatric disorders is characterized by a number of side effects believed to be due to the compounds' inability to selectvely block certain neurochemicals, and not others. ADHD, for example, is a disease affecting 3–6% of school age children, and is also recognized in percentage of adults. Aside from hampering performance at school, and at work, ADHD is a significant risk factor for the subsequent development of anxiety disorders, depression, conduct disorder and drug abuse. Since current treatment regimes require psychostimulants, and since a substantial number of patients (30%) are resistant to stimulants or cannot tolerate their side effects, there is a need for a new drug or class of drugs which treats ADHD and does not have resistance or side effect problems. In addition, methylphenidate, the current drug of choice for the treatment of ADHD, induces a number of side effects; these include anorexia, insomnia and jittery feelings, tics, as well as increased blood pressure and heart rate secondary to the activation of the sympathetic nervous system. However, Methylphenidate also has a high selectivity for the dopamine transporter protein over the norepinephrine transporter protein (DAT/NET Ki ratio of 0.1), which can lead to addiction liability and requires multiple doses per day for optimal efficacy. Thus, there continues to remain a need to develop novel compounds which block reuptake of norephinephrine, dopamine, and serotonin with particular selectivity ratios.

U.S. Pat. No. 3,947,456, discloses tetrahydroisoquinolines which are said to have utility as anti-depressants. U.S. Pat. No. 3,666,763, describes the use of phenyl tetrahydroisoquinoline derivatives as antidepressants and antihypotensives. Canadian Patent Application No. 2,015,114, discloses the use of phenyl tetrahydroisoquinoline derivatives as antidepressants; moreover, described therein are apparently nonselective as to norepinephrine, serotonin and dopamine uptake. UK Patent Application No. 2,271,566, discloses the use of phenyl tetrahydroisoquinoline derivatives as anti-HIV agents. PCT International Application No. WO98/40358 discloses the use of phenyl tetrahydroisoquinoline derivatives to be useful in the treatment of disorders of glucose metabolic pathways. WO97/36876 discloses the use of phenyl tetrahydroisoquinoline derivatives as anti-cancer agents. WO97/23458 also describes 4 phenyl-substituted tetrahydroisoquinolines as NMDA receptor ligands useful for conditions associated with neuronal loss. Phenyl-substituted tetrahydroisoquinolines are also described in Mondeshka et al I1 Farmaco, 1994,49 pp. 475–481.

Nomofensine® which is a 4 phenyl-substituted tetrahydroisoquinoline derivative is known to inhibit the neuronal uptake of dopamine and other catecholamines and has shown clinical efficacy for ADHD. However, long term administration of Nomofensine® results in fatal immune hemolytic anemia. Thus, there continues to remain a need to develop novel compounds which treat ADHD but do not have the serious side effects associated with Nomifensine® or the currently prescribed psychostimulants.

The present invention discloses novel aryl and heteroaryl substituted tetrahydroisoquinoline derivatives compounds which block reuptake of norephinephrine, dopamine, or serotonin, and are usefuil as alternatives to methylphenidate, and known psychostimulants, in the treatment of ADHD and other neurological and psychiatric disorders.

The present inventors have discovered that the claimed compounds which block reuptake of norephinephrine, dopamine, and serotonin with particular selectivity ratios, e.g., being more selective for the norepinephrine transporter (NET) protein than dopamine transporter (DAT) protein or serotonin transporter (SERT) protein (lower Ki for NET than for DAT and SERT). It is postulated that the compounds would therefore be effective as an ADHD treatment with reduced addictive liability profiles. In particular, some of the compounds of this invention are surprisingly and particularly selective for NET over the SERT protein, thus also affording compounds without the known side effect profiles of the selective serotonin reuptake inhibitor (SSRI) class of compounds.

SUMMARY OF THE INVENTION

This invention is directed to a compound of formula (I):

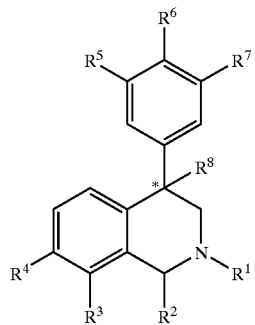

(I)

wherein:

the carbon atom designated * is in the R or S configuration;

$R^1$ is $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, each of which is optionally substituted with from 1 to 3 substituents independently selected at each occurrence thereof from $C_1$–$C_3$ alkyl, halogen, Ar, —CN, —$OR^9$ and —$NR^9R^{10}$;

$R^2$ is H, $C_1$–$C_6$ alkyl, $C_2$–$C_6$ alkenyl, $C_2$–$C_6$ alkynyl, $C_3$–$C_6$ cycloalkyl, $C_4$–$C_7$ cycloalkylalkyl or $C_1$–$C_6$ haloalkyl;

$R^3$ is H, halogen, —$OR^{11}$, —$S(O)_nR^{12}$, —CN, —C(O)$R^{12}$, —C(O)$NR^{11}R^{12}$, $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl and wherein each of $C_1$–$C_6$ alkyl, $C_2$–$C_6$ alkenyl, $C_2$–$C_6$ alkynyl, $C_3$–$C_6$ cycloalkyl and $C_4$–$C_7$ cycloalkylalkyl is optionally substituted with from 1 to 3 substituents independently selected at each occurrence thereof from $C_1$–$C_3$ alkyl, halogen, —CN, —$OR^9$, —$NR^9R^{10}$ and phenyl which is optionally substituted 1–3 times with halogen, cyano, $C_1$–$C_4$ alkyl, $C_1$–$C_4$ haloalkyl, or $C_1$–$C_4$ alkoxy, —CN, —$OR^9$, or —$NR^9R^{10}$;

$R^4$ is aryl selected from phenyl, naphthyl and indenyl, or heteroaryl selected from pyridyl, pyrimidinyl, triazinyl, triazolyl, furanyl, pyranyl, indazolyl, benzimidazolyl, quinolinyl, quinazolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl and thiadiazolyl, wherein the aryl or heteroaryl group is optionally substituted with from 1 to 4 $R^{14}$ substituents;

$R^5$ and $R^6$ and $R^7$ are each independently H or are selected from halogen, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —C(O)$R^{12}$, —C(O)$NR^{11}R^{12}$, $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, and wherein each of $C_1$–$C_6$ alkyl, $C_2$–$C_6$ alkenyl, $C_2$–$C_6$ alkynyl, $C_3$–$C_6$ cycloalkyl and $C_4$–$C_7$ cycloalkylalkyl is optionally substituted with from 1 to 3 substituents independently selected at each occurrence thereof from $C_1$–$C_3$ alkyl, halogen, —CN, —$OR^9$, —$NR^9R^{10}$ and phenyl which is optionally substituted 1–3 times with halogen, cyano, $C_1$–$C_4$ alkyl, $C_1$–$C_4$ haloalkyl, or $C_1$–$C_4$ alkoxy, —CN, —$OR^9$, or —$NR^9R^{10}$; or $R^5$ and $R^6$ may be —O—$C(R^{12})_2$—O—;

$R^8$ is H, halogen or $OR^{11}$;

$R^9$ and $R^{10}$ are each independently H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, —C(O)$R^{13}$, phenyl or benzyl, where phenyl or benzyl is optionally substituted from 1 to 3 times with a substituent selected independently at each occurrence thereof from halogen, cyano, $C_1$–$C_4$ alkyl, $C_1$–$C_4$ haloalkyl and $C_1$–$C_4$ alkoxy, or $R^9$ and $R^{10}$ are taken together with the nitrogen to which they are attached to form a piperidine, pyrrolidine, piperazine, N-methylpiperazine, morpholine or thiomorpholine ring;

$R^{11}$ is H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, —C(O)$R^{13}$, phenyl or benzyl, where phenyl or benzyl is optionally substituted 1 to 3 times with halogen, cyano, $C_1$–$C_4$ alkyl, $C_1$–$C_4$ haloalkyl, or $C_1$–$C_4$ alkoxy, $R^{12}$ is H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, phenyl or benzyl, where phenyl or benzyl is optionally substituted 1 to 3 times with halogen, cyano, $C_1$–$C_4$ alkyl, $C_1$–$C_4$ haloalkyl, or $C_1$–$C_4$ alkoxy, or $R^{11}$ and $R^{12}$ are taken together with the nitrogen to which they are attached to form a piperidine, pyrrolidine, piperazine, N-methylpiperazine, morpholine or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine or thiomorpholine ring;

$R^{13}$ is $C_1$–$C_4$ alkyl, $C_1$–$C_4$ haloalkyl or phenyl;

n is 0, 1, or 2; and, $R^{14}$ is independently selected at each occurrence from a substituent selected from the group: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —C(O)$R^{12}$, —C(O)$NR^{11}R^{12}$, $C_1$–$C_6$ alkyl, $C_2$–$C_6$ alkenyl, $C_2$–$C_6$ alkynyl, $C_3$–$C_6$ cycloalkyl, and $C_4$–$C_7$ cycloalkylalkyl where $C_1$–$C_6$ alkyl, $C_2$–$C_6$ alkenyl, $C_2$–$C_6$ alkynyl, $C_3$–$C_6$ cycloalkyl, $C_4$–$C_7$ cydoalkylalkyl are optionally substituted with 1 to 3 substituents independently selected at each occurrence from the group consisting of $C_1$–$C_3$ alkyl, halogen, Ar, —CN, —$OR^9$, and —$NR^9R^{10}$, or an oxide thereof, a pharmaceutically acceptable salt thereof, a solvate thereof, or prodrug thereof.

DETAILED DESCRIPTION OF THE INVENTION

As used above, and throughout the description of the invention, the following terms, unless otherwise indicated, shall be understood to have the following meanings:—

The term "Alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "Alkenyl" means an aliphatic hydrocarbon group containing a carbon—carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl or propyl are attached to a linear alkenyl chain. Exemplary alkenyl groups include ethenyl, propenyl, n-butenyl, and i-butenyl.

The term "Alkynyl" means an aliphatic hydrocarbon group containing a carbon—carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl or propyl are attached to a linear alkynyl chain. Exemplary alkynyl groups include ethynyl, propynyl, n-butynyl, 2-butynyl, 3-methylbutynyl, and n-pentynyl.

The term "Aryl" means an aromatic monocyclic or multicyclic ring system of 6 to about 14 carbon atoms, preferably of 6 to about 10 carbon atoms. Representative aryl groups include phenyl and naphthyl.

The term "Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen or sulfur. Preferred heteroaryls contain about 5 to 6 ring atoms. The prefix aza, oxa or thia before heteroaryl means that at least a nitrogen, oxygen or sulfur atom, respectively, is present as a ring atom. A nitrogen atom of a heteroaryl is optionally oxidized to the corresponding N-oxide. Representative heteroaryls include pyrazinyl; furanyl; thienyl; pyridyl; pyrimidinyl; isoxazolyl; isothiazolyl; oxazolyl; thiazolyl; pyrazolyl; furazanyl; pyrrolyl; pyrazolyl; triazolyl; 1,2,4-thiadiazolyl; pyrazinyl; pyridazinyl; quinoxalinyl; phthalazinyl; 1(2H)-phthalazinonyl; iniidazo[1,2-a] pyridine; imidazo[2,1-b]thiazolyl; benzofurazanyl; indolyl; azaindolyl; benzimidazolyl; benzothienyl; quinolinyl; imidazolyl; thienopyridyl; quinazolinyl; thienopyrimidyl; pyrrolopyridyl; imidazopyridyl; isoquinolinyl; benzoazaindolyl; azabenzimidazolyl, 1,2,4-triazinyl; benzothiazolyl and the like.

The term "Alkoxy" means an alkyl-O— group wherein the alkyl group is as herein described. Exemplary alkoxy groups include methoxy, ethoxy, n-propoxy, i-propoxy, n-butoxy and heptoxy.

The term "Compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "Cycloalkyl" means a non-aromatic mono- or multicyclic ring system of about 3 to about 7 carbon atoms, preferably of about 5 to about 7 carbon atoms. Exemplary monocyclic cycloalkyl include cyclopentyl, cyclohexyl, cycloheptyl, and the like.

The term "Cycloalkylalkyl" means an cycloalkyl-alkyl-group in which the cycloalkyl and alkyl are as defined herein. Exemplary cycloalkylalkyl groups include cyclopropylmethyl and cyclopentylmethyl.

The term "Halo" or "halogen" means fluoro, chloro, bromo, or iodo.

The term "Haloalkyl" means both branched and straight-chain alkyl substituted with 1 or more halogen, wherein the alkyl group is as herein described.

The term "Haloalkoxy" means a $C_{1-4}$ alkoxy group substituted by at least one halogen atom, wherein the alkoxy group is as herein described.

The term "Substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "Pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example S. M. Berge, et al., "Pharmaceutical Salts," J. Pharm. Sci., 66: p.1-$^{19}$ (1977) and *Remington's Pharmaceutical Sciences*, 17th ed., Mack Publishing Company, Easton, Pa., 1985, p. 1418, which are incorporated herein by reference.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylarnine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "Pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p.309–396, 1985; A Textbook of Drug Design and Development, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference. Examples of prodrugs include, but are not limited to, acetate, formate and benzoate derivatives of alcohol and amine functional groups in the compounds of the invention.

The term "Therapeutically effective amounts" is meant to describe an amount of compound of the present invention effective in increasing the levels of serotonin, norepinephrine or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it; and, the nature and severity of the condition being treated.

The term "Pharmaceutical composition" means a composition comprising a compound of formula (I) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifingal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar— agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

The term "Pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

The term "Pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

PREFERRED EMBODIMENTS

A preferred aspect of the invention is the compound of formula (I) wherein:

$R^1$ is $C_1$–$C_6$ alkyl;

$R^2$ is H, $C_1$–$C_6$ alkyl or $C_1$–$C_6$ haloalkyl;

$R^3$ is H, halogen, —$OR^{11}$, —$S(O)_nR^{12}$, —CN, —C(O)$R^{12}$, $C_1$–$C_6$ alkyl, $C_3$–$C_6$ cycloalkyl or $C_4$–$C_7$ cycloalkylalkyl and wherein each of $C_1$–$C_6$ alkyl, $C_3$–$C_6$ cycloalkyl and $C_4$–$C_7$ cycloalkylalkyl is optionally substituted with from 1 to 3 substituents independently selected at each occurrence thereof from $C_1$–$C_3$ alkyl, halogen, —CN, —$OR^9$, —$NR^9R^{10}$ and phenyl which is optionally substituted 1–3 times with halogen, cyano, $C_1$–$C_4$ alkyl, $C_1$–$C_4$ haloalkyl, or $C_1$–$C_4$ alkoxy, —CN, —$OR^9$, or —$NR^9R^{10}$;

$R^4$ is phenyl, pyridyl, pyrimidinyl, triazinyl, triazolyl, furanyl, pyranyl, indazolyl, benzimidazolyl, quinolinyl, quinazolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, and pyrazolyl, each of which is optionally substituted with from 1 to 4 $R^{14}$;

$R^5$ and $R^6$ and $R^7$ are each independently selected from the group: H, halogen, —$OR^{11}$, —$NR^{11}R^{12}$, —$NR^{11}C(O)R^{12}$, $S(O)_nR^{12}$, —CN, —$C(O)R^{12}$, —$C(O)NR^{11}R^{12}$, $C_1$–$C_6$ alkyl, $C_3$–$C_6$ cycloalkyl or $C_4$–$C_7$ cycloalkylalkyl, and wherein each of $C_1$–$C_6$ alkyl, $C_3$–$C_6$ cycloalkyl and $C_4$–$C_7$ cycloalkylalkyl is optionally substituted with from 1 to 3 substituents independently selected at each occurrence thereof from $C_1$–$C_3$ alkyl, halogen, —CN, —$OR^9$, —$NR^9R^{10}$ and phenyl which is optionally substituted 1–3 times with halogen, cyano, $C_1$–$C_4$ alkyl, $C_1$–$C_4$ haloalkyl, or $C_1$–$C_4$ alkoxy, —CN, —OR$^9$, or —NR$^9$R$^{10}$; or R$^5$ and R$^6$ may be —O—C(R$^{12}$)$_2$—O—; and R$^{14}$ as being independently selected at each occurrence thereof from the group: halogen, —NO$_2$, —OR$^{11}$, —NR$^{11}$R$^{12}$, —S(O)$_n$R$^{12}$, —CN, —C(O)R$^{12}$, $C_1$–$C_6$ alkyl, $C_3$–$C_6$ cycloalkyl, and $C_4$–$C_7$ cycloalkylalkyl where $C_1$–$C_6$ alkyl, $C_3$–$C_6$ cycloalkyl, $C_4$–$C_7$ cycloalkylalkyl are optionally substituted with 1 to 3 substituents independently selected at each occurrence thereof from $C_1$–$C_3$ alkyl, halogen, Ar, —CN, —OR$^9$, or —NR$^9$R$^{10}$.

Another preferred aspect of the invention is the compound of formula (I) wherein:

R$^1$ is methyl, ethyl, propyl or isopropyl;

R$^2$ is H, $C_1$–$C_6$ alkyl or $C_1$–$C_6$ haloalkyl;

R$^3$ is H, halogen, —OR$^{11}$, —S(O)$_2$R$^{12}$, $C_1$–$C_6$ alkyl wherein $C_1$–$C_6$ alkyl is optionally substituted with 1 to 3 substituents independently selected at each occurrence thereof from $C_1$–$C_3$ alkyl, halogen, Ar, —CN, —OR$^9$, or —NR$^9$R$^{10}$;

R$^4$ is pyridyl, pyrimidinyl, triazinyl, triazolyl, furanyl, pyranyl, indazolyl, thienyl, imidazolyl, thiazolyl, purinyl, isothiazolyl, indolyl, pyrrolyl, oxazolyl, isoxazolyl, or pyrazolyl, each of which is optionally substituted with from 1 to 4 R$^{14}$; and R$^5$, R$^6$ and R$^7$ are each independently selected from the group: H, halogen, —OR$^{11}$, —S(O)$_2$R$^{12}$, —NR$^{11}$R$^{12}$, —C(O)R$^{12}$, and $C_1$–$C_6$ wherein $C_1$–$C_6$ alkyl is optionally substituted with 1 to 3 substituents independently selected at each occurrence thereof from $C_1$–$C_3$ alkyl, halogen, Ar, —CN, —OR$^9$, or —NR$^9$R$^{10}$.

Another preferred aspect of the invention is the compound of formula (I) wherein:

R$^1$ is CH$_3$;

R$^2$ and R$^3$ are each H;

R$^5$ and R$^6$ are each independently H, F Cl, OH, OCH$_3$ or CH$_3$;

R$^7$ is H or F; and

R$^8$ is H, OH, or F.

Another preferred aspect of the invention is the compound of formula (I) wherein:

R$^1$ is $C_1$–$C_6$ alkyl, more preferably methyl.

Another preferred aspect of the invention is the compound of formula (I) wherein:

R$^2$ is H, $C_1$–$C_6$ alkyl or $C_1$–$C_6$ haloalkyl, preferably wherein R$^2$ is H or $C_1$–$C_6$ alkyl, more preferably H.

Another preferred aspect of the invention is the compound of formula (I) wherein R$^3$ is H, halogen, —OR$^{11}$, —S(O)$_2$R$^{12}$, $C_1$–$C_6$ alkyl or substituted $C_1$–$C_6$ alkyl, more preferably H.

Another preferred aspect of the invention is the compound of formula (I) wherein:

R$^4$ is optionally substituted aryl, or heteroaryl.

Another more preferred aspect of the invention is the compound of formula (I) wherein:

R$^4$ is pyridyl, pyrimidinyl, triazinyl, triazolyl, furanyl, pyranyl, indazolyl, benzimidazolyl, quinolinyl, quinazolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, thiadiazolyl, phenyl, 2-chlorophenyl, 3-chlorophenyl, 4-chlorophenyl, 2-methoxyphenyl, 3-methoxyphenyl, 4-methoxyphenyl or 4-dimethylaminophenyl, which is optionally substituted 1–4 times with R$^{14}$.

A further more preferred aspect of the invention is the compound of formula (I) wherein:

R$^4$ is selected from the group: 4-methyl-2-furanyl, 5-methyl-2-furanyl, 3-furanyl, 2-thienyl, 3-thienyl, 3,5-dimethyl-4-isoxazolyl, 2-pyridyl, 3-pyridyl, 4-pyridyl, 2-methoxy-3-pyridyl, 6-methoxy-3-pyridyl, 3,5-pyrimidinyl and 2,6-pyrimidinyl.

Another more preferred aspect of the invention is the compound of formula (I) wherein:

R$^5$, R$^6$ and R$^7$ are each independently selected from the group: H, halogen, —OR$^{11}$, —NR$^{11}$R$^{12}$, —, —S(O)$_2$R$^{12}$, —C(O)R$^{12}$, and optionally substituted $C_1$–$C_6$ alkyl.

Another more preferred aspect of the invention is the compound of formula (I) wherein: R$^7$ is H.

Another more preferred aspect of the invention is the compound of formula (I) wherein: R$^5$ and R$^6$ are each independently selected from the group: H, F, Cl, OH, OCH$_3$ and CH$_3$.

Another more preferred aspect of the invention is the compound of formula (I) wherein R$^8$ is H, OH, or F.

Another more preferred aspect of the invention is the compound of formula (I) wherein R$^1$ is $C_1$–$C_6$ alkyl;

R$^2$ is H, $C_1$–$C_6$ alkyl or $C_1$–$C_6$ haloalkyl;

R$^3$ is H, halogen, —OR$^{11}$, —S(O)$_2$R$^{12}$, $C_1$–$C_6$ alkyl or substituted $C_1$–$C_6$ alkyl;

R$^4$ is aryl or heteroaryl; and

R$^5$, R$^6$ and R$^7$ are each independently H, halogen, —OR$^{11}$, —NR$^{11}$R$^{12}$, —S(O)$_2$R$^{12}$, —C(O)R$^{12}$, $C_1$–$C_6$ alkyl or substituted $C_1$–$C_6$ alkyl.

Another more preferred aspect of the invention is the compound of formula (I) wherein:

R$^1$ is methyl;

R$^2$ is H;

R$^3$ is H;

R$^5$ and R$^6$ are each independently H, F, Cl, OH, OMe, or Me;

R$^7$ is H or F;

R$^8$ is H, OH, or F; and

R$^4$ is phenyl, pyridyl, pyrimidinyl, triazinyl, triazolyl, furanyl, pyranyl, indazolyl, thienyl, imidazolyl, thiazolyl, purinyl, isothiazolyl, indolyl, pyrrolyl, oxazolyl, isoxazolyl, or pyrazolyl, each of which is optionally and independently substituted from 1–4 times with R$^{14}$.

Another more preferred aspect of the invention is the compound of formula (I) wherein:

R$^1$ is methyl;

R$^2$ is H;

R$^3$ is H;

R$^5$ and R$^6$ are each H, F or CH$_3$;

R$^7$ is H;

R$^8$ is H; and

R$^4$ is phenyl, 2-chlorophenyl, 3-chlorophenyl, 4-chlorophenyl, 2-methoxyphenyl, 3-methoxyphenyl, 4-methoxyphenyl, 4-dimethylaminophenyl, 4-methyl-2-furanyl, 5-methyl-2-furanyl and 3-furanyl, 2-thienyl and 3-thienyl, isoxazolyl which is 3,5-dimethyl-4-isoxazolyl, 2-pyridyl, 3-pyridyl, 4-pyridyl, 2-methoxy-3-pyridyl and 6-methoxy-3-pyridyl or 3,5-pyrimidinyl or 2,6-pyrimidinyl.

Another more preferred aspect of the invention is the compound of formula (I) wherein the carbon atom designated * is in the R configuration.

Another more preferred aspect of the invention is the compound of formula (I) wherein the carbon atom designated * is in the S configuration.

Another preferred aspect of the invention is a mixture of stereoisomeric compounds of formula (I) wherein * is in the S or R configuration.

Within these embodiments, the selection of a particular preferred substituent at any one of $R^1$–$R^8$ does not affect the selection of a substituent at any of the others of $R^1$–$R^8$. That is, preferred compounds provided herein have any of the preferred substituents at any of the positions. For example, as described hereinabove, $R^1$ is preferably $C_1$–$C_6$ alkyl; the selection of $R^1$ as any one of $C_1$, $C_2$, $C_3$, $C_4$, $C_5$ or $C_6$ alkyl, does not limit the choice of $R^2$ in particular to any one of H, $C_1$–$C_6$ alkyl or $C_1$–$C_6$ haloalkyl. Rather, for $R^1$ as any of $C_1$, $C_2$, $C_3$, $C_4$, $C_5$ or $C_6$ alkyl, $R^2$ is any of H, $C_1$, $C_2$, $C_3$, $C_4$, $C_5$ or $C_6$ alkyl or $C_1$, $C_2$, $C_3$, $C_4$, $C_5$ or $C_6$ haloalkyl. Similarly, the selection of $R^2$ as any of H, $C_1$, $C_2$, $C_3$, $C_4$, $C_5$ or $C_6$ alkyl or $C_1$, $C_2$, $C_3$, $C_4$, $C_5$ or $C_6$ haloalkyl does not limit the selection of $R^3$ in particular to any one of H, halogen, —$OR^{11}$, —$S(O)_nR^{12}$, —CN, —$C(O)R^{12}$, $C_1$–$C_6$ alkyl, $C_3$–$C_6$ cycloalkyl, $C_4$–$C_7$ cycloalkylalkyl or substituted $C_4$–$C_7$ cycloalkylalkyl.

More preferred compounds of the invention are those with the following substituents:

TABLE A (I)

| $R^1$ | $R^2$ | $R^3$ | $R^4$ | $R^5$ | $R^6$ | $R^7$ | $R^8$ |
|---|---|---|---|---|---|---|---|
| Me | H | H | phenyl | H | H | H | H |
| Me | H | H | 2-chlorophenyl | H | H | H | H |
| Me | H | H | 3-chlorophenyl | H | H | H | H |
| Me | H | H | 4-chlorophenyl | H | H | H | H |
| Me | H | H | 2-methoxyphenyl | H | H | H | H |
| Me | H | H | 3-methoxyphenyl | H | H | H | H |
| Me | H | H | 4-methoxyphenyl | H | H | H | H |
| Me | H | H | 4-dimethylaminophenyl | H | H | H | H |
| Me | H | H | 4-methyl-2-furanyl | H | H | H | H |
| Me | H | H | 5-methyl-2-furanyl | H | H | H | H |
| Me | H | H | 3-furanyl | H | H | H | H |
| Me | H | H | 2-thienyl | H | H | H | H |
| Me | H | H | 3-thienyl | H | H | H | H |
| Me | H | H | 3,5-dimethyl-4-isoxazole | H | H | H | H |
| Me | H | H | 2-pyridyl | H | H | H | H |
| Me | H | H | 3-pyridyl | H | H | H | H |
| Me | H | H | 4-pyridyl | H | H | H | H |
| Me | H | H | 3-pyridyl | F | F | H | H |
| Me | H | H | 2-methoxy-3-pyridyl | H | H | H | H |
| Me | H | H | 6-methoxy-3-pyridyl | H | H | H | H |
| Me | H | H | 3,5-pyrimidinyl | H | H | H | H |
| Me | H | H | 3,5-pyrimidinyl | F | F | H | H |
| Me | H | H | 3,5-pyrimidinyl | H | Me | H | H |
| Me | H | H | 2,6-pyrimidinyl | H | H | H | H |
| Me | H | H | 3,5-dimethyl-4-isoxazole | H | OMe | H | H |
| Me | H | H | 2-pyridyl | H | Ome | H | H | wherein the carbon atom designated * is in the R or S configuration. That is, the specific compounds provided herein include:

4,7-diphenyl-2-methyl-1,2,3,4-tetrahydroisoquinoline;
7-(2-chloro)phenyl-2-methyl-4-phenyl-1,2,3,4-tetrahydroisoquinoline;
7-(3-chloro)phenyl-2-methyl-4-phenyl-1,2,3,4-tetrahydroisoquinoline;
7-(4-chloro)phenyl-2-methyl-4-phenyl-1,2,3,4-tetrahydroisoquinoline;
7-(2-methoxy)phenyl-2-methyl-4-phenyl-1,2,3,4-tetrahydroisoquinoline;
7-(3-methoxy)phenyl-2-methyl-4-phenyl-1,2,3,4-tetrahydroisoquinoline;
7-(4-methoxy)phenyl-2-methyl-4-phenyl-1,2,3,4-tetrahydroisoquinoline;
7-(4-N,N-dimethylamino)phenyl-2-methyl-4-phenyl-1,2,3,4-tetrahydroisoquinoline;
7-[(4-methyl)-2-thienyl]-2-methyl-4-phenyl-1,2,3,4-tetrahydroisoquinoline;
7-[(5-methyl)-2-furanyl]-2-methyl-4-phenyl-1,2,3,4-tetrahydroisoquinoline;
7-(3-furanyl)-2-methyl-4-phenyl-71,2,3,4-tetrahydroisoquinoline;
2-methyl-4-phenyl-7-(2-thienyl)-1,2,3,4-tetrahydroisoquinoline;
2-methyl-4-phenyl-7-(3-thienyl)-1,2,3,4-tetrahydroisoquinoline;
7-[(3,5-dimethyl)-4-isoxazole]-2-methyl-4-phenyl-1,2,3,4-tetrahydroisoquinoline;
2-methyl-4-phenyl-7-(2-pyridyl)-1,2,3,4-tetrahydroisoquinoline;
2-methyl-4-phenyl-7-(3-pyridyl)-1,2,3,4-tetrahydroisoquinoline;
2-methyl-4-phenyl-7-(4-pyridyl)-1,2,3,4-tetrahydroisoquinoline;
4-(3,4-difluoro)phenyl-2-methyl-7-(3-pyridyl)-1,2,3,4-tetrahydroisoquinoline;
7-[(2-methoxy)-3-pyridyl]-2-methyl-4-phenyl-1,2,3,4-tetrahydroisoquinoline;
7-[(6-methoxy)-3-pyridyl]-2-methyl-4-phenyl-1,2,3,4-tetrahydroisoquinoline;
2-methyl-4-phenyl-7-(3,5-pyrimidyl)-1,2,3,4-tetrahydroisoquinoline;
4-(3,4-difluoro)phenyl-2-methyl-7-(3,5-pyrrndyl)-1,2,3,4-tetrahydroisoquinoline;
4-(4-methyl)phenyl-2-methyl-7-(3,5-pyrimidyl)-1,2,3,4-tetrahydroisoquinoline;
2-methyl-4-phenyl-7-(2,6-pyrimidyl)-1,2,3,4-tetrahydroisoquinoline;
7-(2,5-dimethyl-4-isoxazole)-4-(4-methoxy)phenyl-2-methyl-1,2,3,4-tetrahydroisoquinoline; and
4-(4-methoxy)phenyl-2-methyl-7-(2-pyridyl)-1,2,3,4-tetrahydroisoquinoline or an oxide thereof, a pharmaceutically acceptable salt thereof, a solvate thereof, or a prodrug thereof.

Another preferred aspect of the invention is a mixture of compounds of formula (I) wherein the compound of formula (I) is radiolabeled, i.e., wherein one or more of the atoms described are replaced by a radioactive isotope of that atom (e.g., C replaced by $^{14}C$ and H replaced by $^3H$). Such compounds have a variety of potential uses, e.g., as standards and reagents in determining the ability of a potential pharmaceutical to bind to neurotransmitter proteins.

Another aspect of the invention is a therapeutically effective amount of the compound (I) and a pharmaceutically acceptable carrier.

Another aspect of the invention is a method of treating a disorder which is created by or is dependent upon decreased availability of serotonin, norepinephrine or dopamine, which comprises administering to a patient in need of such treatment a therapeutically effective amount of a compound of formula (I), or a pharmaceutically acceptable salt thereof.

Another aspect of the invention is a method of treating a disorder which is created by or is dependent upon decreased availability of serotonin, norepinephrine or dopamine, which comprises administering to a patient in need of such treatment a therapeutically effective amount of a compound of formula (I), or a pharmaceutically acceptable salt thereof and a therapeutically effective amount of a serotonin 1A receptor antagonist, or pharmaceutically acceptable salt thereof.

Another aspect of the invention is a method of treating a disorder which is created by or is dependent upon decreased availability of serotonin, norepinephrine or dopamine, which comprises administering to a patient in need of such treatment a therapeutically effective amount of a compound of formula (I), or a pharmaceutically acceptable salt thereof and a therapeutically effective amount of a compound selected from the group consisting of WAY 100135 and spiperone, or pharmaceutically acceptable salt thereof.

WAY 100135 (N-(t-butyl)-3-[a-(2-methoxyphenyl) piperazin-1-yl]-2-phenylpropanamide) is disclosed in Abou-Gharbia et al., U.S. Pat. No. 4,988,814,as having an affinity for the 5-HT$_{1A}$ receptor. Also, Cliffe et al., J. Med. Chem. 36, 1509–10 (1993) showed that the compound is a 5-HT$_{1A}$ antagonist. Spiperone (8-[4-(4-fluorophenyl)-4-oxobutyl]-1-phenyl-1,3,8-triazaspiro[4,5]decan-4-one) is a well-known compound, and is diclosed in U.S. Pat. Nos. 3,155,669 and 3,155,670. The activity of Spiperone as a 5-HT$_{1A}$ antagonist is shown in Middlemiss et al., Neurosci. and Biobehav. Rev. 16, 75–82 (1992).

Another aspect of the invention is a method of treating a disorder which is created by or is dependent upon decreased availability of serotonin, norepinephrine or dopamine, which comprises administering to a patient in need of such treatment a therapeutically effective amount of a compound of formula (I), or a pharmaceutically acceptable salt thereof and a therapeutically effective amount of a selective neurokinin-1 receptor antagonist, or pharmaceutically acceptable salt thereof.

Neurokinin-1 receptor antagonists of use in combination a compound of formula (I) in the present invention, are fully described, for example, in U.S. Pat. Nos. 5,373,003, 5,387,595, 5,459,270, 5,494,926, 5,162,339, 5,232,929, 5,242,930, 5,496,833, 5,637,699; PCT International Patent Publication Nos. WO 90/05525, 90/05729, 94/02461, 94/02595, 94/03429,94/03445, 94/04494, 94/04496, 94/05625, 94/07843, 94/08997, 94/10165, 94/10167, 94/10168, 94/10170, 94/11368, 94/13639, 94/13663, 94/14767,94/ 15903, 94/19320, 94/19323, 94/20500, 91/09844, 91/18899, 92/01688, 92/06079, 92/12151,92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304,96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in U.K. Patent Application Nos. 2 266 529, 2 268 931, 2 269 170, 2 269 590, 2 271 774, 2 292 144, 2 293168, 2 293 169, and 2 302 689; European Patent Publication Nos. EP 0 360 390, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 699 674, 0 707 006, 0 708 101, 0 709 375, 0 709 376, 0 714 891, 0 723 959, 0733 632 and 0 776 893. The preparation of such compounds are fuly described in the aforementioned patents and publications.

Another aspect of the invention is a method of treating a disorder which is created by or is dependent upon decreased availability of serotonin, norepinephrine or dopamine, which comprises administering to a patient in need of such treatment a therapeutically effective amount of a compound of formula (I), or a pharmaceutically acceptable salt thereof and a therapeutically effective amount of a norepinephrine precursor, or pharmaceutically acceptable salt thereof.

Another aspect of the invention is a method of treating a disorder which is created by or is dependent upon decreased availability of serotonin, norepinephrine or dopamine, which comprises administering to a patient in need of such treatment a therapeutically effective amount of a compound of formula (I), or a pharmaceutically acceptable salt thereof and a therapeutically effective amount of a compound selected from L-tyrosine and L-phenylalanine, or pharmaceutically acceptable salt thereof.

Another aspect of the invention is a method of treating a disorder referred to in the above-mentioned embodiments, wherein the disorder is selected from the group: attention deficit disorder, hyperactivity disorder, anxiety, depression, post-traumatic stress disorder, supranuclear palsy, eating disorders, obsessive compulsive disorder, analgesia, nicotine addiction, panic attacks, Parkinsonism and phobia, obesity, late luteal phase syndrome or narcolepsy, cocaine addiction, amphetamine addiction, and psychiatric symptoms anger such as, rejection sensitivity, and lack of mental or physical energy.

Another aspect of the invention is a method of inhibiting synaptic norepinephrine uptake in a patient in need thereof comprising administering a therapeutically effective inhibitory amount of a compound of formula (I).

Another aspect of the invention is a method of inhibiting synaptic serotonin uptake in a patient in need thereof comprising administering a therapeutically effective inhibitory amount of a compound of formula (I).

Another aspect of the invention is a method of inhibiting synaptic dopamine uptake in a patient in need thereof comprising administering a therapeutically effective inhibitory amount of a compound of formula (I).

Another aspect of the invention is a therapeutic method described herein wherein the (+)-stereoisomer of the compound of formula (I) is employed.

Another aspect of the invention is a therapeutic method described herein wherein the (−)-stereoisomer of the compound of formula (I) is employed.

Another aspect of the invention is a kit comprising a compound of formula (I) and at least one compound selected from the group consisting of: a serotonin 1A receptor antagonist compound, a selective neurokinin-1 receptor antagonist compound, and a norepinephrine precursor compound.

Another aspect of the invention is a method of treating depression in a patient in need thereof comprising inhibiting synaptic serotonin and norepinephrine uptake by administering a therapeutically effective inhibitory amount of a compound of formula (I) which functions as both a serotonin and norepinephrine uptake inhibitor.

Another aspect of the invention is a method of treating depression in a patient in need thereof comprising inhibiting synaptic serotonin and dopamine uptake by administering a therapeutically effective inhibitory amount of a compound of formula (I) which functions as both a serotonin and dopamine uptake inhibitor.

Another aspect of the invention is a method of treating depression in a patient in need thereof comprising inhibiting synaptic dopamine and norepinephrine uptake by administering a therapeutically effective inhibitory amount of a compound of formula (I) which functions as both a dopamine and norepinephrine uptake inhibitor.

Another aspect of the invention is a method for inhibiting serotonin uptake in mammals which comprises administering to a mammal requiring increased neurotransmission of serotonin a pharmaceutically effective amount of a compound of formula (I).

Another aspect of the invention is a method for inhibiting dopamine uptake in patients which comprises administering to a mammal requiring increased neurotransmission of dopamine a pharmaceutically effective amount of a compound of formula (I).

Another aspect of the invention is a method for inhibiting norepinephrine uptake in patients which comprises administering to a mammal requiring increased neurotransmission of norepinephrine a pharmaceutically effective amount of a compound of formula (I).

Another aspect of the invention is a method of suppressing the desire of humans to smoke comprising administering to a human in need of such suppression an effective dose, to relieve the desire to smoke, of a compound of formula (I).

Another aspect of the invention is a method of suppressing the desire of humans to consume alcohol comprising administering to a human in need of such suppression an effective dose, to relieve the desire to consume alcohol, of a compound of formula (I).

It is appreciated that certain feactures of the invention, which are, for clarity, described in the context of separate embodiments, may also be provided in combination in a single embodiment. Conversely, various feactures of the invention which are, for brevity, described in the context of a single embodiment, may also be provided seperately or in any suitable subcombination.

Preparation of Compounds of the Invention

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by R. C. Larock in Comprehensive Organic Transformations, VCH publishers, 1989.

A compound of formula (I) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

The novel tetrahydroisoquinoline reuptake inhibitors of formula (I) of this invention can be prepared by the general scheme outlined below (Scheme 1). The $R^1$-substituted N-benzyl amines of formula (III) may be purchased from commercial sources, or alternatively, obtained from a simple reductive amination protocol. Thus, carbonyl containing compounds of formula (II) may be treated with $H_2N-R^1$ in lower alkyl alcoholic solvents (preferably methanol or ethanol) at temperatures at or below room temperature. The resulting imine may be reduced most commonly with alkaline earth borohydrides (preferably sodium borohydride) to provide the desired amine intermediates.

Treatment of intermediates of formula (III) with intermediates of formula (V) cleanly generates the alkylation products of formula (VI). The alkylation reactions may be run under a wide variety of conditions familiar to one skilled in the art of organic synthesis. Typical solvents include acetonitrile, toluene, diethyl ether, tetrahydrofuran, dimethylsulfoxide, dimethylformamide, methylene chloride, and lower alkyl alcohols including ethanol. The reactions may be successfully run at temperatures ranging from 0° C. up to the boiling point of the solvent employed. Reaction progress is conventionally monitored by standard chromatographic and spectroscopic methods. The alkylation reaction is optionally run with the addition of a non-nucleophilic organic base such as, but not limited to, pyridine, triethylamine and diisopropyl ethylamine.

The aforementioned intermediate of formula (V) is conveniently purchased from commercial sources or prepared via treatment of an optionally substituted acetophenone of formula (IV) with common brominating agents such as, but not limited to, bromine, NBS, or tetrabutylammonium tribromide which readily affords the desired bromoacetophenones of formula (V). These reactions are optimally conducted in acetic acid or methylene chloride with methanol used as a co-solvent for the tribromide reagent with reaction temperatures at or below room temperature. Another embodiment of this methodology would include the use of chloroacetophenone compounds of formula (V).

The acetophenones of formula (IV) are also available from commercial sources or are conveniently obtained via several well known methods, including the treatment of the corresponding benzoic acid intermediates with two stoichiometric equivalents of methyllithium (see, e.g., Jorgenson, M. J., *Organic Reactions,* 1970, 18, pg. 1). Alternatively, one may treat the corresponding benzaldehydes with an alkyl-Grignard (for example, MeMgBr) or alkyl-lithium (for example, MeLi) nucleophile follwed by routine oxidation to the ketone (see, e.g., Larock, R. C., *Comprehensive Organic Transformations,* VCH Publishers, New York, 1989, p. 604).

Reductions of compounds of formula (VI) to the benzyl alcohols of formula (VII) proceeds with many reducing agents including, for example, sodium borohydride, lithium borohydride, borane, diisobutylaluminum hydride, and lithium aluminum hydride. The reductions are carried out for a period of time between 1 hour to 3 days at room temperature or elevated temperature up to the reflux point of the solvent employed. If borane is used, it may be employed as a complex for example, but not limited to, borane-methyl sulfide complex, borane-piperidine complex, or borane-tetrahydrofuran complex. One skilled in the art will understand the optimal combination of reducing agents and reaction conditions needed or may seek guidance from the text of Larock, R. C. (see above).

Compounds of formula (VII) may be cyclized to the tetrahydroisoquinoline compounds of formula (VIII) of this invention by brief treatment with a strong acid. Suitable acids include, but are not limited to, concentrated sulfuric acid, polyphosphoric acid, methanesulfonic acid and trifluoroacetic acid. The reactions are run neat or in the optional presence of a co-solvent such as, for example, methylene chloride or 1,2-dichloroethane. The cyclizations may be conducted at temperatures ranging from 0° C. up to the reflux point of the solvent employed. One skilled in the art of heterocyclic chemistry will readily understand these conditions or may consult the teachings of Mondeshka, et al., Il Farmaco, 1994, 49, 475–480 or Venkov, et al., Synthesis, 1990, 253–255. Cyclizations may also be effected by treatment of compounds of formula (VII) with strong Lewis acids, such as for example, aluminum trichloride typically in halogenated solvents such as methylene chloride. One skilled in the art will be familiar with the precedent taught by Kaiser, et al., *J. Med. Chem.,* 1984, 27, 28–35 and Wyrick, et al., *J. Med. Chem.,* 1981, 24, 1013–1015.

Finally, the target compounds of formula (I) of this invention may be prepared by treatment of compounds of formula (VIII, X=Br, or I) with an aryl or heteroaryl boronic acids or aryl or heteroaryl boronic acid esters where Y is equivalent to $B(OH)_2$ or $B(OR^a)(OR^b)$ (where $R^a$ and $R^b$ are lower alkyl, ie. $C_1$–$C_6$, or taken together, $R^a$ and $R^b$ are lower alkylene, ie. $C_2$–$C_{12}$) in the presence of a metal catalyst with or without a base in an inert solvent to give isoquinoline compounds of formula (XIII). Metal catalysts include, but are not limited to, salts or phosphine complexes of Cu, Pd, or Ni (eg. $Cu(OAc)_2$, $PdCl_2(PPh_3)_2$, $NiCl_2(PPh_3)_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloaalkanes (preferably methylene chloride). Prefered reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao, et al., *Tetrahedron,* 1994, 50, 979–988.

Compounds of formula (I) may be obtained in enantiomerically pure (R) and (S) form by crystallization with chiral salts as well known to one skilled in the art, or alternatively, may be isolated through chiral HPLC employing commercially available chiral columns.

Compounds of formula (I) wherein $R^8$=OH, of this invention may be prepared according to the teaching of Kihara, et al., *Tetrahedron,* 1992, 48, 67–78, and Blomberg, et al., *Synthesis,* 1977, p. 18–30. Thus ketone compounds of formula (VI) which possess an ortho-iodide may be treated with strong bases, such as, but not limited to, lower alkyl ($C_{1-6}$) lithium bases (preferably t-BuLi or n-BuLi) to afford the anticipated halogen-metal exchange followed by intramolecular Barbier cyclization to generate compounds of formula (I) wherein $R^8$=OH. Inert is solvents such as dialkyl ethers (preferably diethyl ether), cyclic ethers (preferably tetrahydrofuran or 1,4-dioxane), etc. are necessary, and reaction temperatures are kept low (−78° C. to −25° C.) to avoid by-products. Alternatively, halogen-metal exchange may also be effected in the presence of zerovalent nickel, in which case N,N-dialkylformamides (preferably dimethylformamide) serve as ideal solvents. This cyclization is best performed when X=Br to avoid over-reduction or intermolecular reactivity. Additionally, compounds of formula (I) wherein $R^8$=OH, may be readily alkylated (vide supra) to afford compounds formula (I) wherein $R^8$=$OR^{11}$. Finally, further treatment of compounds of formula (I) wherein $R^8$=OH, with a halogenating reagent or specifically a fluorinating reagent such as, but not limited to, diethylaminosulfur trifluoride (DAST), readily provides compounds of formula (I) wherein $R^8$=F. Further reference may be gained from the review of Hudlicky, *Organic Reactions,* 1985, 35, p. 513–637.

The contents of the above-cited disclosures are incorporated herein by reference.

Scheme 1

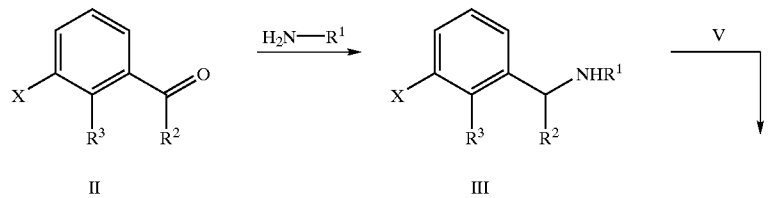

II            III

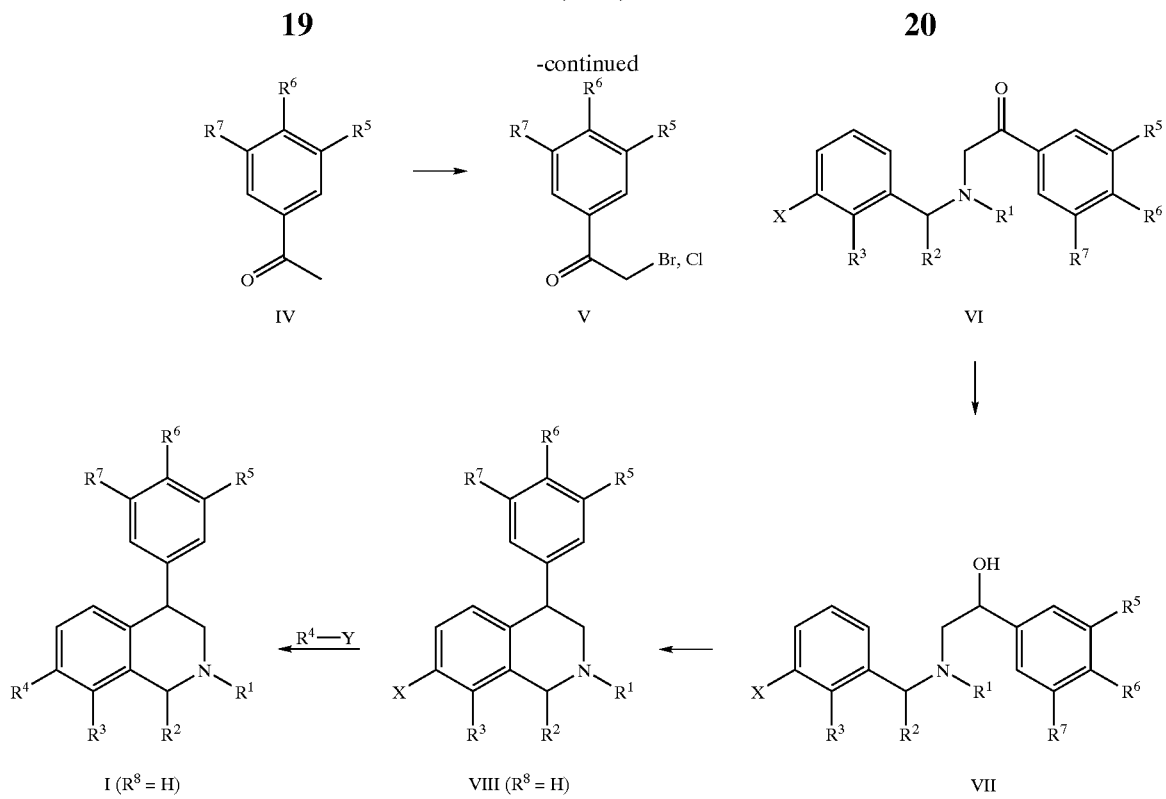

It will be appreciated that compounds useful according to the present invention may contain asymmetric centres. These asymmetric centres may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

Radiolabelled compounds of the invention are synthesized by a number of means well known to those of ordinary skill in the art, e.g., by using starting materials incorporating therein one or more radioisotopes.

This invention provides compositions containing the compounds described herein, including, in particular, pharmaceutical compositions comprising therapeutically effective amounts of the compounds and pharmaceutically acceptable carriers.

It is a further object of the invention to provide kits having a plurality of active ingredients (with or without carrier) which, together, may be effectively utilized for carrying out the novel combination therapies of the invention.

It is another object of the invention to provide a novel pharmaceutical compositions which is effective, in and of itself, for utilization in a beneficial combination therapy because it includes a plurality of active ingredients which may be utilized in accordance with the invention.

The invention also provides kits or single packages combining two or more active ingredients useful in treating the disease. A kit may provide (alone or in combination with a pharmaceutically acceptable diluent or carrier), the compound of formula (I) and the additional active ingredient (alone or in combination with diluent or carrier) selected from a serotonin 1A receptor antagonist, a selective neurokinin-1 receptor antagonist, and a norepinephrine precursor.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula (I).

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine and serotonin uptake and are therefore believed to be useful in treating a disorder which is created by or is dependent upon decreased availability of serotonin, norepinephrine or dopamine. Although the compounds of the formula (I) inhibit synaptic norepinephrine, dopamine and serotonin uptake, in any individual compound these inhibitory effects may be manifested at the same or vastly different concentrations or doses. As a result, some compounds of the formula (I) are useful in treating such a disorder at doses at which synaptic norepinephrine uptake may be substantially inhibited but at which synaptic serotonin uptake or dopamine uptake is not substantially inhibited, or visa versa. Also, some compounds of the formula (I) are useful in treating such a disorder at doses at which synaptic dopamine uptake may be substantially inhibited but at which synaptic norepinephrine or serotonin uptake is not substantially inhibited, or visa versa. And, conversely, some compounds of the formula (I) are useful in treating such a disorder at doses at which synaptic serotonin uptake may be substantially inhibited but at which synaptic norepinephrine or dopamine uptake is not substantially inhibited, or visa versa. Other compounds of formula (I) are useful in treating such a disorder at doses at which synaptic norepinephrine, dopamine and serotonin uptake are substantially inhibited.

The concentrations or doses at which a test compound inhibits synaptic norepinephrine, dopamine and serotonin uptake is readily determined by the use of standard assay and techniques well known and appreciated by one of ordinary skill in the art. For example, the degree of inhibition at a particular dose in rats can be determined by the method of Dudley, et al., [J. Pharmacol. Exp. Ther. 217, 834–840 (1981)], which is incorporated by reference.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine and serotonin uptake. The therapeutically effective inhibitory dose can be readily determined by those skilled in the art by using conventional range finding techniques and analagous results obtained in the test systems described above.

Compounds of this invention provide a particularly beneficial therapeutic index relative to other compounds available for the treatment of similar disorders. Without intending to be limited by theory, it is believed that this is due, at least in part, to some of the compounds' having higher binding affinities, e.g. their ability to be selective, for the norepinephrine transporter protein ("NET") over the transporters for other neurochemicals, e.g., the dopamine transporter protein ("DAT") and the serotonin transporter protein ("SERT").

Binding affinities are demonstrated by a number of means well known to ordinarily skilled artisans, including, without limitation, those described in the Examples section hereinbelow. Briefly, for example, protein-containing extracts from cells, e.g., HEK293E cells, expressing the transporter proteins are incubated with radiolabelled ligands for the proteins. The binding of the radioligands to the proteins is reversible in the presence of other protein ligands, e.g., the compounds of this invention; said reversability, as described below, provides a means of measuring the compounds' binding affinities for the proteins (Ki). A higher Ki value for a compound is indicative that the compound has less binding affinity for a protein than is so for a compound with a lower Ki; conversely, lower Ki values are indicative of greater binding affinities.

Accordingly, the difference in compound selectivity for proteins is indicated by a lower Ki for the protein for which the compound is more selective, and a higher Ki for the protein for which the compound is less selective. Thus, the higher the ratio in Ki values of a compound for protein A over protein B, the greater is the compounds' selectivity for the latter over the former (the former having a higher Ki and the latter a lower Ki for that compound). Compounds provided herein induce fewer side effects during therapeutic usage because of their selectivity for the norepinephrine transporter protein, as indicated by the ratios of their Ki's for binding to NET over those for binding to other transporter proteins, e.g., DAT and SERT. Generally, some of the compounds of this invention have a Ki ratio for DAT/NET of at least about 2:1; generally also have a SERT/NET ratio of at least about 20:1.

Moreover, in vivo assessment of the activity of compounds at the NE and DA transporters is, for example, by determining their ability to prevent the sedative effects of tetrabenazine (TBZ) (see, e.g., G. Stille, Arzn. Forsch 14:534–537, 1964, the contents of which are incorporated herein by reference). Randomized and coded doses of test compounds are administered to mice, as is then a dose of tetrabenazine. Animals are then evaluated for antagonism of tetrabenazine-induced exploratory loss and ptosis at specified time intervals after drug administration. Exploratory activity is, for example, evaluated by placing the animal in the center of a circle and then evaluating the amount of time it takes for the animal to intersect the circle's perimeter—generally, the longer it takes for the animal to make this intersection, the greater is its loss of exploratory activity. Furthermore, an animal is considered to have ptosis if its eyelids are at least 50% closed. Greater than 95% of the control (vehicle-treated) mice are expected to exhibit exploratory loss and ptosis; compound-related activity is then calculated as the percentage of mice failing to respond to the tetrabenazine challenge dose, with therapeutically more effective compounds expected to better at reducing loss of exploratory behavior and ptosis.

Accordingly, this invention provides methods of treating subjects afflicted with various neurological and psychiatric disorders by administering to said subjects a dose of a pharmaceutical composition provided herein. Said disorders include, without limitation, attention deficit-hyperactivity disorder, anxiety, depression, post-traumatic stress disorder, supranuclear palsy, feeding disorders, obsessive compulsive disorder, analgesia, smoking cessation, panic attacks, Parkinson's and phobia. The compounds provided herein are particularly useful in the treatment of these and other disorders due, at least in part, to their ability to selectively bind to the transporter proteins for certain neurochemicals with a greater affinity than to the transporter proteins for other neurochemicals.

The compounds of the invention, their methods or preparation and their biological activity will appear more clearly from the examination of the following examples which are presented as an illustration only and are not to be considered as limiting the invention in its scope.

EXAMPLES

Compounds listed in Table 1 below (examples 1–26) were made according to the synthetic schemes set forth hereinabove, and have the melting points, or have been identified by mass spectroscopy (MS), as set forth in the table; where a compound is an oil or a solid, it is listed as such therein.

TABLE I

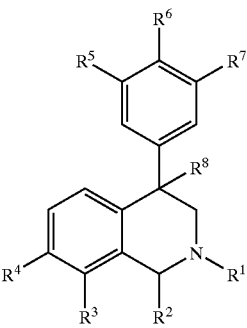

| Ex. | R1 | R2 | R3 | R4 | R5 | R6 | R7 | R8 | Mp (° C.) |
|---|---|---|---|---|---|---|---|---|---|
| 1 | Me | H | H | phenyl | H | H | H | H | Oil, MS |
| 2 | Me | H | H | 2-chlorophenyl | H | H | H | H | Oil, MS |
| 3 | Me | H | H | 3-chlorophenyl | H | H | H | H | Oil, MS |
| 4 | Me | H | H | 4-chlorophenyl | H | H | H | H | Oil, MS |
| 5 | Me | H | H | 2-methoxyphenyl | H | H | H | H | Oil, MS |
| 6 | Me | H | H | 3-methoxyphenyl | H | H | H | H | Oil, MS |
| 7 | Me | H | H | 4-methoxyphenyl | H | H | H | H | Oil, MS |
| 8 | Me | H | H | 4-dimethylaminophenyl | H | H | H | H | 89–90 |
| 9 | Me | H | H | 4-methyl-2-furanyl | H | H | H | H | Oil, MS |
| 10 | Me | H | H | 5-methyl-2-furanyl | H | H | H | H | 63–66 |
| 11 | Me | H | H | 3-furanyl | H | H | H | H | 188–189 |
| 12 | Me | H | H | 2-thienyl | H | H | H | H | Oil, MS |
| 13 | Me | H | H | 3-thienyl | H | H | H | H | Oil, MS |
| 14 | Me | H | H | 3,5-dimethyl-4-isoxazole | H | H | H | H | Oil, MS |
| 15 | Me | H | H | 2-pyridyl | H | H | H | H | Oil, MS |
| 16 | Me | H | H | 3-pyridyl | H | H | H | H | Oil, MS |
| 17 | Me | H | H | 4-pyridyl | H | H | H | H | Oil, MS |
| 18 | Me | H | H | 3-pyridyl | F | F | H | H | 98–99.5 |

TABLE I-continued

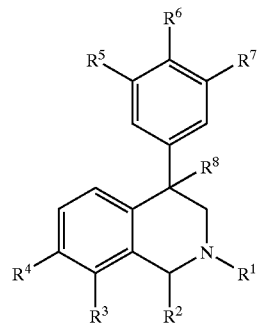

| Ex. | R1 | R2 | R3 | R4 | R5 | R6 | R7 | R8 | Mp (° C.) |
|---|---|---|---|---|---|---|---|---|---|
| 19 | Me | H | H | 2-methoxy-3-pyridyl | H | H | H | H | Oil, MS |
| 20 | Me | H | H | 6-methoxy-3-pyridyl | H | H | H | H | Oil, MS |
| 21 | Me | H | H | 3,5-pyrimidinyl | H | H | H | H | Oil, MS |
| 22 | Me | H | H | 3,5-pyrimidinyl | F | F | H | H | Solid |
| 23 | Me | H | H | 3,5-pyrimidinyl | H | Me | H | H | 146–147.5 |
| 24 | Me | H | H | 2,6-pyrimidinyl | H | H | H | H | Oil, MS |
| 25 | Me | H | H | 3,5-dimethyl-4-isoxazole | H | OMe | H | H | Oil, MS |
| 26 | Me | H | H | 2-pyridyl | H | Ome | H | H | Oil, MS |

Example 1

Preparation of 4,7-diphenyl-2-methyl-1,2,3,4-tetrahydroisiquinoline

Step A: A solution of 3-bromobenzaldehyde (12.03 g, 7.3 ml, 65.0 mmol) and methylamine (40% aqueous, 7.3 ml, 84.5 mmol) in methanol (70 ml) was stirred for 10 minutes at room temperature under a nitrogen atmosphere yielding a faint yellow solution. Sodium borohydride ($NaBH_4$, 1.23 g, 35.5 mmol) was added portionwise over five minutes and the resulting solution stirred for one hour. Solid 2-chloroacetophenone (10.1 g, 65.0 mmol) was added to the reaction mixture and the solution stirred an one hour at room temperature. When the reaction was complete by thin-layer chromatography (3:7 ethyl acetate/hexanes), a full equivalent of sodium borohydride (2.46 g, 65.0 mmol) was slowly added and the reaction stirred for twelve hours. The reaction was quenched with water (50 ml) and extracted with methylene chloride (3×40 ml). The combined organic extracts were washed with water (2×40 ml), dried over anhydrous sodium sulfate, filtered, and concentrated in vacuo. Chromatography ($SiO_2$, 800 g, 3:7 ethyl acetate/hexanes) afforded the product as a viscous yellow liquid (8.95 g): $^1H$ NMR ($CDCl_3$, 300 MHz) δ 7.47-7.21 (m, 8H), 4.76 (dd, 1H, J=4.4, 9.9 Hz), 3.91 (br s, 1H), 3.60 (q, 2H), 2.56 (m, 2H), 2.31 (s, 3H).

Step B: The product from Step A (3.50 g, 11.6 mmol) was stirred in methylene chloride (500 ml) at 0° C. To this was added 98% sulfuric acid (50 ml) dropwise over 30 minutes. The reaction was stirred an additional 30 minutes until thin-layer chromatography (2:1 ethyl acetate/hexanes) indicated the reaction complete. The solution was diluted with water (50 ml) and basified with the slow addition of 25% $NH_4OH$. The product was extracted with methylene chloride (3×50 ml) and the combined organic layers washed with water (2×50 ml), dried over anhydrous magnesium sulfate, filtered and concentrated in vacuo. Chromatography ($SiO_2$, 300 g, 2:1 ethyl acetate/hexanes) afforded the product as a viscous light yellow oil (0.98 g): $^1H$ NMR ($CDCl_3$, 300 MHz) δ 7.32-7.14 (m, 7H), 6.74 (m, 1H), 4.20 (t, 1H, J=7.6 Hz), 3.65 (q, 2H), 3.02 (dd, 1H, J=5.7, 12.0 Hz), 2.52 (dd, 1H, J=8.8, 11.5 Hz), 2.42 (s, 3H). $^{13}C$ NMR ($CDCl_3$, 75 MHz) δ 144.1, 137.5, 136.3, 131.1, 129.4, 129.0, 128.4, 126.7, 120.0, 61.5, 58.0, 45.8, 45.5. HRMS-CI calcd. for $C_{16}H_{16}NBr$ $[M+H]^+$ 302.0540. Found 302.0535. The free base was converted to its maleate salt by dissolving the oil in a minimal amount of absolute ethanol, adding one equivalent of maleic acid and placing the solution at −30° C. until crystal formation occurred. Filtration yielded a white solid: mp 173.0–174.0° C. Anal. Calcd. For $C_{20}H_{20}NBrO_4$: C, 57.43; H, 4.829; N, 3.358. Found: C, 57.27; H 4.89; N, 3.27.

Step C: The product from Step B (0.100 g, 0.33 mmol) in ethylene glycol dimethyl ether (1 ml) which had been previously sparged under nitrogen for ten minutes was treated with 2N $Na_2CO_3$ (0.40 ml) followed by phenyl boronic acid (51 mg, 0.41 mmol) and a catalytic amount of $Pd(PPh_3)_4$ (39 mg, 0.033 mmol). The reaction heated to 70° C. with agitation for eight hours during which time the solution slowly turned orange/brown. The reaction was diluted with 1 ml of water and extracted with methylene chloride (7×1 ml). The combined organic layer was concentrated in vacuo. Chromatography ($SiO_2$, 60 g, 2:1 ethyl acetate/hexanes) afforded the pure product as an oil (50.2 mg): $^1H$ NMR ($CDCl_3$, 300 MHz) δ 7.58-7.22 (m, 12H), 6.94 (m, 1H), 4.31 (t, 1H, J=5.9 Hz), 3.76 (q, 2H), 3.07 (dd, 1H, J=5.9, 11.4 Hz), 2.61 (dd, 1H, J=8.8, 11.4 Hz), 2.46 (s, 3H). HRMS-CI calcd. for $C_{22}H_{22}N$ $[M+H]^+$ 300.1752. Found 300.1763.

Examples 2–8 were prepared according to the method exemplified for the preparation of Example 1.

Example 2

Preparation of 7-(2-chloro)phenyl-2-methyl-4-phenyl-1,2,3,4-tetrahydroisoquinoline The product from Example 1, Step B (0.200 g, 0.66 mmol) and 2-chlorophenyl boronic acid (157 mg, 1.00 mmol) afforded, after chromatography, the pure product as an oil (123 mg): $^1H$ NMR ($CDCl_3$, 300 MHz) δ 7.47-6.92 (m, 12H), 4.32 (t, 1H, J=8.1 Hz), 3.74 (q, 2H), 3.06 (dd, 1H, J=6.2, 11.7 Hz), 2.62 (dd, 1H, J=8.5, 11.4 Hz), 2.45 (s, 3H). HRMS-CI calcd. for $C_{22}H_{21}NCl$ $[M+H]^+$ 334.1362. Found 334.1355.

Example 3
Preparation of 7-(3-chloro)phenyl-2-methyl-4-phenyl-1,2,3,4-tetrahydroisoquinoline The product from Example 1, Step B (0.100 g, 0.33 mmol) and 3-chlorophenyl boronic acid (65 mg, 0.41 mmol) afforded, after chromatography, the pure product as an oil (60.8 mg): $^1$H NMR (CDCl$_3$, 300 MHz) δ 7.55 (m, 1H), 7.45-7.21 (m, 10H), 6.94 (m, 1H), 4.31(t, 1H, J=8.1 Hz), 3.79 (q, 2H), 3.09 (dd, 1H, J=5.5, 11.4 Hz), 2.65 (dd, 1H, J=8.8, 11.7 Hz), 2.48 (s, 3H). HRMS-CI calcd. for C$_{22}$H$_{21}$NCl [M+H]$^+$ 334.1362. Found 334.1374.

Example 4
Preparation of 7-(4-chloro)phenyl-2-methyl-4-phenyl-1,2,3,4-tetrahydroisoquinoline The product from Example 1, Step B (0.200 g, 0.66 mmol) and 4-chlorophenyl boronic acid (157 mg, 1.00 mmol) afforded, after chromatography, the pure product as an oil (116 mg): $^1$H NMR (CDCl$_3$, 300 MHz) δ 7.51-7.21 (m, 11H), 6.94 (m, 1H), 4.30 (t, 1H, J=5.8 Hz), 3.75 (q, 2H), 3.07 (dd, 1H, J=5.9, 11.8 Hz), 2.60 (dd, 1H, J=8.8, 11.8 Hz), 2.46 (s, 3H). HRMS-CI calcd. for C$_{22}$H$_{21}$NCl[M+H]$^+$ 334.1362. Found 334.1366.

Example 5
Preparation of 7-(2-methoxy)phenyl-2-methyl-4-phenyl-1,2,3,4-tetrahydroisoquinoline The product from Example 1, Step B (0.200 g, 0.66 mmol) and 2-methoxyphenyl boronic acid (152 mg, 1.00 mmol) afforded, after chromatography, the pure product as an oil (121 mg): $^1$H NMR (CDCl$_3$, 300 MHz) δ 7.34-7.20 (m, 9H), 7.03-6.88 (m, 3H), 4.30 (t, 1H, J=5.9 Hz), 3.80 (s, 3H), 3.73 (q, 2H), 3.06 (dd, 1H, J= 5.5, 11.4 Hz), 2.60 (dd, 1H, J=5.5, 11.4 Hz), 2.44 (s, 3H). HRMS-CI calcd. for C$_{23}$H$_{24}$NO [M+H]$^+$ 330.1858. Found 330.1874.

Example 6
Preparation of 7-(3-methoxy)phenyl-2-methyl-4-phenyl-1,2,3,4-tetrahydroisoquinoline The product from Example 1, Step B (0.200 g, 0.66 mmol) and 3-methoxyphenyl boronic acid (152 mg, 1.00 mmol) afforded, after chromatography, the pure product as an oil (112 mg): $^1$H NMR (CDCl$_3$, 300 MHz) δ 7.36-6.85 (m, 12H), 4.30 (t, 1H, J=5.8 Hz), 3.85 (s, 3H), 3.80 (q, 2H), 3.10 (dd, 1H, J=5.8, 11.7 Hz), 2.67 (dd, 1H, J=8.7, 11.0 Hz), 2.48 (s, 3H). HRMS-CI calcd. for C$_{23}$H$_{24}$NO [M+H]$^+$ 330.1858. Found 330.1848.

Example 7
Preparation of 7-(4-methoxy)phenyl-2-methyl-4-phenyl-1,2,3,4-tetrahydroisoquinoline The product from Example 1, Step B (0.200 g, 0.66 mmol) and 4-methoxyphenyl boronic acid (152 mg, 1.00 mmol) afforded, after chromatography, the pure product as an oil (114 mg): $^1$H NMR (CDCl$_3$, 300 MHz) δ 7.53-6.90 (m, 12H), 4.30 (t, 1H, J=5.8 Hz), 3.84 (s, 3H), 3.73 (q, 2H), 3.06 (dd, 1H, J=6.6, 11.9 Hz), 2.61 (dd, 1H, J=8.8, 11.7 Hz), 2.46 (s, 3H). HRMS-CI calcd. for C$_{23}$H$_{24}$NO [M+H]$^+$ 330.1858. Found 330.1871.

Example 8
Preparation of 7-(4-N,N-dimethylamino)phenyl-2-methyl-4-phenyl-1,2,3,4-tetrahydroisoquinoline The product from Example 1, Step B (0.200 g, 0.66 mmol) and 4-N,N-dimethylaminophenyl boronic acid (165 mg, 1.00 mmol) afforded, after chromatography, the pure product as an oil that crystallized upon standing (103 mg): mp 89–90° C., $^1$H NMR (CDCl$_3$, 300 MHz) δ 7.47 (m, 2H) 7.33-7.21 (m, 7H), 6.90 (m, 1H), 6.79 (m, 2H), 4.29 (t, 1H, J=5.8 Hz), 3.84 (s, 3H), 3.74 (q, 2H), 3.05 (dd, 1H, J=5.5, 11.4 Hz), 2.98 (s, 6H), 2.60 (dd, 1H, J=8.7, 11.3 Hz), 2.45 (s, 3H). HRMS-CI calcd. for C$_{24}$H$_{27}$N$_2$ [M+H]$^+$ 343.2174. Found 343.2174.

Example 9
Preparation of 7-[(4-methyl-2)thienyl]-2-methyl-4-phenyl-1,2,3,4-tetrahydroisoquinoline Step A: To a solution of oxalyl chloride (8.72 ml, 99.33 mmol) in anhydrous methylene chloride (240 ml) at −78° C. was added anhydrous dimethyl sulfoxide (14.12 ml, 199 mmol). After stirring for 15 minutes, 3-iodobenzyl alcohol was dissolved in 50 ml anhydrous methylene chloride and added dropwise to the chilled solution via syringe over four minutes. After 30 minutes, triethylamine (41.04 ml, 295 mmol) was added and stirred at −78° C. for one hour before being warmed to 0° C. After one hour, the reaction was poured into water (1 L) and the layers separated. The aqueous layer was extracted with diethyl ether (4×150 ml) and the combined organic extracts dried over anhydrous magnesium sulfate, filtered and concentrated in vacuo. Chromatography (SiO$_2$, 300 g, 2:8 ethyl acetate/hexanes) yielded the product as an oil (26.83 g): $^1$H NMR (CDCl$_3$, 300 MHz) δ 9.92 (s, 1H), 8.21 (s, 1H), 7.95 (d, 1H, J=7.0 Hz), 7.85 (d, 1H, J=7.5 Hz), 7.29 (t, 1H, J=8 Hz).

Step B: The product from Step A (26.83 g, 0.115 mol) was stirred with aqueous methylamine (12.8 ml, 148 mmol) in methanol (115 ml) for 1 hour. Sodium borohydride (2.18 g, 0.058 mol) was added portionwise, and the resulting mixture stirred at room temperature overnight. Methanol was removed in vacuo, and distilled water (250 ml) added to the residue. The resulting solution was extracted with ethyl acetate (3×100 ml). The combined organic extracts were dried over anhydrous sodium sulfate, filtered, and concentrated in vacuo to yield an oil (28.61 g): $^1$H NMR (CDCl$_3$, 300 MHz) δ 7.69 (s, 1H), 7.58 (d, 1H, J=9.1 Hz), 7.27 (d, 1H, J=7.6 Hz), 7.05 (t, 1H, J=7.9 Hz), 3.69 (s, 2H), 2.43 (s, 3H).

Step C: To the product from Step B (28.6 g, 0.116 mol) in methylene chloride (194 ml) was added triethylamine (13.7 mL, 0.116 mol) and the solution chilled to 0° C. 2-Bromoacetophenone (28.86 g, 0.145 mol) in methylene chloride (182 mL) was added over 20 minutes and the reaction stirred at room temperature for 3 hours, quenched with water (500 ml) and the layers separated. The resulting aqueous layer was extracted with methylene chloride (5×100 ml) and the combined organic layer was dried over anhydrous sodium sulfate, filtered, and concentrated in vacuo to yield a yellow oil. Column chromatography (SiO$_2$, 1.5 kg, 1:1 ethyl acetate/hexanes) afforded the pure product (16.05 g). $^1$H NMR (CDCl$_3$, 300 MHz) δ 7.95 (d, 2H, J=8.4 Hz), 7.72 (s, 1H), 7.58 (m, 2H), 7.46 (t, 2H, J=7.5 Hz), 7.32 (d, 1H, J=7.7 Hz), 7.05 (t, 1H, J=7.7 Hz), 3.81 (s, 2H), 3.62 (s, 2H), 2.37 (s, 3H).

Step D: The product from Step C (16.05 g, 44 mmol) in methanol (70 ml) was chilled to 0° C. and sodium borohydride (1.53 g, 40.5 mmol) added portionwise to the solution. The reaction was stirred at 0° C. for two hours and the methanol removed in vacuo. Distilled water (500 ml) was added to the residue and the solution was extracted with methylene chloride (3×100 ml). The combined organic extracts were dried over anhydrous sodium sulfate, filtered, and concentrated in vacuo to yield the product as a pale yellow solid (14.86 g) which was used without further purification. $^1$H NMR (CDCl$_3$, 300 MHz) δ 7.67 (s, 1H), 7.62 (d, 1H, J=8.1 Hz), 7.29 (m, 6H), 7.08 (t, 1H, J=7.7 Hz), 4.76 (dd, 1H, J=4.0, 9.9 Hz), 3.90 (s, 1H), 3.67 (d, 1H, J=13.18 Hz), 3.48 (d, 1H, J=13.18 Hz), 2.57 (m, 2H), 2.37 (s, 3H).

Step E: The product from Step D (13.48 g, 36.7 mmol) in methylene chloride (148 ml) was chilled to 0° C. followed by addition of AlCl$_3$, (10.77 g, 80.7 mmol) in methylene chloride (100 ml). The reaction was stirred for one hour at 0° C., warmed to room temperature and stirred for 1 hour. The solution was slowly poured onto ice/water and the layers separated. The aqueous phase was extracted with methylene chloride (4×100 ml) and the combined organic extracts dried over anhydrous sodium sulfate, filtered, and concentrated in vacuo to yield a red oil. Column chromatography (SiO$_2$, 1:1 ethyl acetate/hexanes) afforded the product as a yellow oil (5.59 g): $^1$H NMR (CDCl$_3$, 300 MHz) δ 7.40 (s, 1H), 7.37 (d, 1H, J=8.0 Hz), 7.23 (m, 5H), 6.61 (d, 1H, J=8.4 Hz), 4.20 (t, 1H, J=7.2 Hz), 3.69 (d, 1H, J=15.2 Hz), 3.57 (d, 1H, J=15.2 Hz), 3.02 (dd, 1H, J=5.8, 11.5 Hz), 2.54 (dd, 1H, J=8.6, 11.6 Hz), 2.42 (s, 3H).

Step F: The product from Step E (0.25 g, 0.72 mmol) in ethylene glycol dimethyl ether (3 ml), which had been previously sparged under nitrogen for ten minutes was treated with 2N Na$_2$CO$_3$ (1.6 ml) and 4-methylthiophene-2-boronic acid (152 mg, 1.07 mmol). A catalytic amount of Pd(PPh$_3$)$_4$ (83 mg, 0.072 mmol) was added and the reaction heated to reflux for four hours until thin-layer chromatography (2:1 ethyl acetate in hexanes) indicated the reaction complete. The reaction was cooled, quenched with saturated sodium bicarbonate (50 ml) and extracted with diethyl ether (4×25 ml). The combined organic extracts were dried over anhydrous sodium sulfate, filtered and concentrated in vacuo to yield the product as a yellow oil. Chromatography (SiO$_2$, 50 g, 1:1 ethyl acetate/hexanes) afforded the pure product as a yellow oil (134 mg): $^1$H NMR (CDCl$_3$, 300 MHz) δ 7.20 (m, 6H), 7.01 (s, 1H), 6.78 (t, 2H, J=7.5 Hz), 4.20 (t, 1H, J=7.0 Hz), 3.72 (d, 1H, J=14.65 Hz), 3.57 (d, 1H, J=14.65 Hz), 2.98 (dd, 1H, J=5.5, 10.6 Hz), 2.49 (dd, 1H, J=8.6, 11.5 Hz), 2.38 (s, 3H), 2.20 (s, 3H). HRMS-CI calcd for C$_{21}$H$_{22}$NS [M+H]$^+$ 320.1473. Found 320.1472.

Examples 10–17 were prepared according to the method exemplified for the preparation of Examples 1, 9.

Example 10

Preparation of 7-[(5-methyl-2)furanyl]-2-methyl-4-phenyl-1,2,3,4-tetrahydroisoquinoline The product from Example 9, Step E (0.30 g, 0.86 mmol) and 5-methylfuran-2-boronic pinacol ester (268 mg, 1.29 mmol) afforded, after chromatography, the pure product as an orange oil which crystallized upon standing (188 mg): mp 63.0–66.0° C. $^1$H NMR (CDCl$_3$, 300 MHz)δ 7.27 (m, 7H), 6.86 (d, 1H, J=8.1 Hz), 6.47 (d, 1H, J=3.3 Hz), 6.03 (d, 1H, J=2.2 Hz), 4.27 (t, 1H, J=7.0 Hz), 3.79 (d, 1H, J=14.46 Hz), 3.64 (d, 1H, J=14.46 Hz), 3.05 (dd, 1H, J=6.8, 11.5 Hz), 2.56 (dd, 1H, J=8.8, 11.4 Hz), 2.44 (s, 3H), 2.36 (s, 3H). HRMS-CI calcd for C$_{21}$H$_{22}$NO [M+H]$^+$ 304.1701. Found 304.1700.

Example 11

Preparation of 7-(3-furanyl)-2-methyl-4-phenyl-1,2,3,4-tetrahydroisoquinoline

The product from Example 1, Step B (0.100 g, 0.33 mmol) and 3-furan boronic acid (46 mg, 0.41 mmol) afforded, after chromatography, the pure product as a solid (48.7 mg): mp 188.0–189.0° C. (dec). $^1$H NMR (CDCl$_3$, 300 MHz) δ 7.69 (s, 1H), 7.46 (m, 1H), 7.33-7.19 (m, 7H), 6.87 (m, 1H), 6.66 (m, 1H), 4.29 (t, 1H, J=8.4 Hz), 3.73 (q, 2H), 3.06 (dd, 1H, J=5.9, 11.4 Hz), 2.57 (dd, 1H, J=8.7, 11.3 Hz), 2.45 (s, 3H). HRMS-CI calcd. for C$_{20}$H$_{20}$NO [M+H]$^+$ 290.1545. Found 290.1558.

Example 12

Preparation of 2-methyl-4-phenyl-7-(2-thienyl)-1,2,3,4-tetrahydroisoquinoline

The product from Example 1, Step B (0.100 g, 0.33 mmol) and 2-thiophene boronic acid (53 mg, 0.41 mmol) afforded, after chromatography, the pure product as an oil (68.6 mg): $^1$H NMR (CDCl$_3$, 300 MHz) δ 7.33-7.19 (m, 9H), 7.06 (m, 1H), 6.87 (m, 1H), 4.28 (t, 1H, J=8.0 Hz), 3.73 (q, 2H), 3.06 (dd, 1H, J=5.5, 11.7 Hz), 2.58 (dd, 1H, J=8.8, 11.3 Hz), 2.45 (s, 3H). HRMS-CI calcd. for C$_{20}$H$_{20}$NS [M+H]$^+$ 306.1316. Found 306.1321.

Example 13

Preparation of 2-methyl-4-phenyl-7-(3-thienyl)-1,2,3,4-tetrahydroisoquinoline

The product from Example 1, Step B (0.100 g, 0.33 mmol) and 3-thiophene boronic acid (53 mg, 0.41 mmol) afforded, after chromatography, the pure product as an oil (62.8 mg): $^1$H NMR (CDCl$_3$, 300 MHz) δ 7.41-7.21 (m, 10H), 6.90 (m, 1H), 4.29 (t, 1H, J=6.2 Hz), 3.74 (q, 2H), 3.05 (dd, 1H, J=5.8, 11.3 Hz), 2.59 (dd, 1H, J=8.7, 11.3 Hz), 2.46 (s, 3H). HRMS-CI calcd. for C$_{20}$H$_{20}$NS [M+H]$^+$ 306.1316. Found 306.1303.

Example 14

Preparation of 7-[(3,5-dimethyl4-isoxazole]-2-methyl-4-phenyl-1,2,3,4-tetrahydroisoquinoline The product from Example 9, Step E (0.25 g, 0.72 mmol) and 3,5-dimethylisoxazole-4-boronic acid (151 mg, 1.07 mmol) afforded, after chromatography, the product as a yellow oil which was further purified by reverse phase high pressure liquid chromatography on a C$_{18}$ column using acetonitrile/water as eluent (109 mg): $^1$H NMR (CDCl$_3$, 300 MHz) δ 7.28 (m, 5H), 6.94 (d, 3H, J=5.1 Hz), 4.30 (t, 1H, J=7.1 Hz), 3.80 (d, 1H, J=15.0 Hz), 3.65 (d, 1H, J=15.0 Hz), 3.08 (dd, 1H, J=5.7, 11.5 Hz), 2.61 (dd, 1H, J=8.8, 11.7 Hz), 2.46 (s, 3H), 2.39 (s, 3H), 2.26 (s, 3H). HRMS-CI calcd. for C$_{21}$H$_{23}$N$_2$O [M+H]$^+$ 319.1810. Found 319.1817.

Example 15

Preparation of 2-methyl-4-phenyl-7-(2-pyridyl)-1,2,3,4-tetrahydroisoquinoline

The product from Example 9, Step E (0.50 g, 1.43 mmol) in dimethylformamide (10 ml) was treated with pinacol diborane (400 mg, 1.58 mmol), potassium acetate (420 mg, 4.28 mmol) and [1,1'-bis(diphenylphosphino)ferrocene] dichloropalladium(II), complex with dichloromethane (1:1) (120 mg, 0.15 mmol). The mixture was heated to 80° C. for two hours, cooled, and 2-bromopyridine (450 mg, 2.85 mmol), 2N Na$_2$CO$_3$ (14.25 ml), and [1,1'-bis(diphenylphosphino)ferrocene] dichloropalladium(II), complex with dichloromethane (1:1) (60 mg, 0.075 mmol) added. The solution was heated to 80° C. overnight, cooled to room temperature, and extracted with diethyl ether (8×20 ml). The combined organic extracts were washed with water (3×25 ml) and brine (1×25 ml), dried over anhydrous magnesium sulfate, filtered and concentrated in vacuo to yield the product as an oil. Chromatography (SiO$_2$, 100 g, 5% methanol/ethyl acetate) afforded the product as a an oil which was further purified by reverse phase high pressure liquid chromatography on a C$_{18}$ column using acetonitrile/water as eluent (31 mg): $^1$H NMR (CDCl$_3$, 300 MHz) δ 8.67 (d, 1H, J=5.5 Hz), 7.71 (m, 3H), 7.26 (m, 6H), 6.98 (d, 1H, J=8.0 Hz), 4.33 (t, 1H, J=7.2 Hz), 3.86 (d, 1H, J=14.83 Hz), 3.70 (d, 1H, J=14.83 Hz), 3.08 (dd, 1H, J=5.8, 11.4 Hz), 2.60 (dd, 1H, J=8.6, 11.5 Hz), 2.46 (s, 3H). HRMS-CI calcd. for C$_{21}$H$_{21}$N, [M+H]$^+$ 301.1705. Found 301.1690.

Example 16
Preparation of 2-methyl-4-phenyl-7-(3-pyridyl)-1,2,3,4-tetrahydroisoquinoline The product from Example 1, Step B (0.100 g, 0.33 mmol) and 3-pyridine boronic acid (51 mg, 0.41 mmol) afforded, after chromatography, the pure product as an oil (67.2 mg): $^1$H NMR (CDCl$_3$, 300 MHz) δ 8.83(m, 1H), 8.56 (m, 1H), 7.84 (m, 1H), 7.36-7.22 (m, 8H), 6.98 (m, 1H), 4.32 (t, 1H, J=5.9 Hz), 3.77 (q, 2H), 3.08 (dd, 1H, J=4.8, 10.7 Hz), 2.61 (dd, 1H, J=8.8, 11.7 Hz), 2.47 (s, 3H). HRMS-CI calcd. for C$_{21}$H$_{21}$N$_2$ [M+H]$^+$ 301.1705. Found 301.1688.

Example 17
Preparation of 2-methyl-4-phenyl-7-(4-pyridyl)-1,2,3,4-tetrahydroisoquinoline The product from Example 9, Step E (0.37 g, 1.06 mmol) and 4-pyridyl boronic acid (196 mg, 1.59 mmol) afforded the product as a yellow oil which was further purified by reverse phase high pressure liquid chromatography on a C$_1$ g column using acetonitrile/water as eluent (31 mg): $^1$H NMR (CDCl$_3$, 300 MHz) δ 8.63 (d, 2H, J=4.6 Hz), 7.48 (d, 2H, J=4.7 Hz), 7.29 (m, 7H), 7.00 (d, 1H, J=7.7 Hz), 4.33 (t, 1H, J=7.2 Hz), 3.86 (d, 1H, J=15.0 Hz), 3.70 (d, 1H, J=15.0 Hz), 3.09 (dd, 1H, J=5.5, 11.4 Hz), 2.63 (dd, 1H, J=8.6, 11.5 Hz), 2.48 (s, 3H). HRMS-CI calcd. for C$_{21}$H$_{21}$N$_2$ [M+H]$^+$ 301.1705. Found 301.1679.

Example 18
Preparation of 4-(3,4-difluoro)phenyl-2-methyl-7-(3-pyridyl)-1,2,3,4-tetrahydroisoquinoline Step A: To 3,4-difluoroacetophenone (15.0 g, 96.0 mmol) in methylene chloride (840 ml) was added tetrabutylammonium tribromide (48.6 g, 101 mmol). The resulting solution was stirred at room temperature for 48 hours. Concentration in vacuo afforded an orange liquid which was dissolved in ethyl acetate (100 ml) and washed with water (2×40 ml) to remove remaining tetrabutylammonium tribromide. The organic layer was dried over anhydrous sodium sulfate, filtered, and concentrated in vacuo yielding a crude yellow liquid (30.3 g). After 12 hours at 0° C., a solid formed in the yellow oil; vacuum filtration followed by water washes (2×50 ml) afforded the product as a white solid (12.2 g): mp 30.0–31.0° C. $^1$H NMR (CDCl$_3$, 300 MHz) δ 7.87-7.76 (m, 2H), 7.34-7.25 (m, 1H), 4.38 (s, 2H).

Step B: A solution of 3-bromobenzaldehyde (12.03 g, 7.3 ml, 65.0 mmol) and methylamine (40% aqueous, 7.3 ml, 84.5 mmol) in methanol (70 ml) was stirred for 10 minutes at room temperature. Sodium borohydride (1.23 g, 35.5 mmol) was added portionwise over five minutes and the solution stirred for one hour. The product from Step A (15.4 g, 65.0 mmol) was added to the reaction mixture and the reaction stirred for one hour. When the reaction was complete by thin-layer chromotography (3:7 ethyl acetate/hexanes), a fill equivalent of sodium borohydride (2.46 g, 65.0 mmol) was slowly added and the reaction stirred for twelve hours. The reaction was quenched with water (50 ml) and the solution was extracted with methylene chloride (3×40 ml). The combined organic extracts were washed with water (2×40 ml), dried over anhydrous sodium sulfate, filtered, and concentrated in vacuo. Chromatography (SiO$_2$, 800 g, 3:7 ethyl acetate/hexanes) afforded the product as a viscous yellow oil, (4.55 g): $^1$H NMR (CDCl$_3$, 300 MHz) δ 7.45-7.39 (m, 2H), 7.26-7.02 (m, 4H), 4.70 (t, 1H, J=6.6 Hz), 3.96 (br s, 1H), 3.60 (q, 2H), 2.52 (m, 2H), 2.31 (s, 3H).

Step C: To the product from Step B (4.55 g, 11.6 mmol) in methylene chloride (500 ml) at 0° C., was added 98% sulfuric acid (50 ml) dropwise over 30 minutes. The reaction was stirred at for 30 minutes until thin-layer chromatography (2:1 ethyl acetate/hexanes) indicated the reaction completion. The reaction was diluted with water (50 ml) and the solution slowly basified with 25% NH$_4$OH. The product was extracted with methylene chloride (3×50 ml) and the combined organic layers washed with water (2×50 ml), dried over anhydrous magnesium sulfate, filtered and concentrated in vacuo. Chromatography (SiO$_2$, 300 g, 2:1 ethyl acetate/hexanes) afforded the product as a viscous light yellow oil (1.34 g): $^1$H NMR (CDCl$_3$, 300 MHz) δ 7.26-6.89 (m, 5H), 6.74 (m, 1H), 4.13 (t, 1H, J=7.6 hz), 3.62 (q, 2H), 2.93 (dd, 1H, J=5.5, 11.7 Hz), 2.55 (dd, 1H, J=7.3, 11.3 Hz), 2.41 (s, 3H). HRMS-CI calcd. for C$_{16}$H$_{15}$NBrF$_2$ [M+H]$^+$ 338.0356. Found 338.0340.

Step D: The product from Step C (0.800 g, 2.64 mmol) and 3-pyridyl boronic acid (111 mg, 0.9 mmol) afforded, after chromatography, the pure product as pink solid (0.545 mg): mp 98–99.5° C., $^1$H NMR (CDCl$_3$, 300 MHz) δ 8.83 (m, 1H), 8.58 (m, 1H), 7.84 (m, 1H), 7.57 (m, 1H), 7.37-6.97 (m, 6H), 4.25 (t, 1H, J=6.2 Hz), 3.74 (s, 2H), 3.74 (q, 2H), 3.00 (dd, 1H, J=5.5, 11.4 Hz), 2.62 (dd, 1H, J=7.0, 11.4 Hz), 2.45 (s, 3H). HRMS-CI calcd. for C$_{21}$H$_{19}$N$_2$F$_2$ [M+H]$^+$ 337.1516. Found 337.1527.

Example 19
Preparation of 7-[(2-methoxy)-3-pyridyl)-2-methyl-4-phenyl-1,2,3,4-tetrahydroisoquinoline Step A: 3-Iodo-2-methoxypyridine (3.0 g, 12.8 mmol) in anhydrous tetrahydrofuran (42 ml) was treated with triisopropyl borate (3.7 ml, 16 mmol) cooled to −100° C. in a liquid nitrogen/diethyl ether bath. To the cooled flask was added N-butyllithium/hexanes (10 ml, 16 mmol) dropwise via syringe. The solution was stirred for 90 minutes, warmed to room temperature, and stirred overnight. The reaction was quenched with 1N HCl (52 ml), stirred for 1 hour and neutralized to pH 8 with 50% NaOH. The basic solution was extracted with ethyl acetate (4×50 ml) and the combined organic extracts dried over anhydrous sodium sulfate, filtered, and concentrated in vacuo to yield the product as a brown oil. Chromatography (SiO$_2$, 125 g, 1:9 ethyl acetate/hexanes) afforded the pure product as a white solid (0.225 g): $^1$H NMR (d$_6$-DMSO, 300 MHz) δ 8.19 (dd, 1H, J=2,2, 5,1 Hz), 7.88 (m, 3H), 6.97 (dd, 1H, J=5.1, 7.0 Hz), 3.87 (s, 3H).

Step B: The product from Example 9, Step E (0.37 g, 1.06 mmol) and the product from Example 19, Step A (220 mg, 1.44 mmol) were combined as described in the synthesis of Example 1, Step C to afford, after chromatography, the product as an oil which was further purified by reverse phase high pressure liquid chromatography on a C$_{18}$ column using acetonitrile/water as eluent (165 mg, 52% yield): $^1$H NMR (CDCl$_3$, 300 MHz) δ 8.14 (dd, 1H, J=2.0, 4.9 Hz), 7.59 (dd, 1H, J=1.8, 7.3 Hz), 7.28 (m, 7H), 6.94 (m, 2H), 4.30 (t, 1H, J=7.0 Hz), 3.96 (s, 3H), 3.80 (d, 1H, J=15.0 Hz), 3.68 (d, 1H, J=15.0 Hz), 3.06 (dd, 1H, J=5.5, 11.4 Hz), 2.62 (dd, 1H, J=8.4, 11.3 Hz), 2.45 (s, 3H). HRMS-CI calcd. for C$_{22}$H$_{23}$N$_2$O [M+H]$^+$ 331.1810. Found 331.1829.

Example 20
Preparation of 7-[(6-methoxy)-3-pyridyl]-2-methyl-4-phenyl-1,2,3,4-tetrahydroisoquinolne Step A: 3-Bromo-6-methoxypyridine (2.0 g, 11.6 mmol) in anhydrous tetrahydrofuran (28 ml) was treated with triisopropyl borate (3.35 ml, 14.5 mmol) and cooled to −100° C. in a liquid nitrogen/diethyl ether bath. To the cooled flask was added N-butyllithium/hexanes (8 ml, 12.8 mmol) dropwise with a syringe. The reaction was stirred for 90 minutes then warmed to room temperature overnight. The reaction was quenched with of 1N HCl (47 ml), stirred for 1 hour and neutralized to pH 8 with 50% NaOH. The basic solution was extracted with ethyl acetate (4×50 ml) and the combined organic extracts dried over anhydrous sodium sulfate, filtered and concentrated in vacuo to yield the product as a white solid. The solid was washed with diethyl ether, filtered and dried to yield the product as a white solid (0.860): $^1$H NMR (d$_6$-DMSO, 300 MHz) δ 8.52 (dd, 1H, J=2.2 Hz), 8.11 (s, 2H), 8.00 (dd, 3H, J=2.1, 8.3 Hz), 6.76 (d, 1H, J=8.0 Hz), 3.85 (s, 3H).

Step B: The product from Example 9, Step E (0.50 g, 1.43 mmol) and the product from Example 20, Step A (294 mg, 1.92 mmol) were combined as described for the synthesis of Example 1, Step C to afford, after chromatography, the product as an oil (292 mg): $^1$H NMR (CDCl$_3$, 300 MHz) δ 8.14 (dd, 1H, J=2.0, 4.9 Hz), 7.59 (dd, 1H, J=1.8, 7.3 Hz), 7.28 (m, 7H), 6.94 (m, 2H), 4.30 (t, 1H, J=7.0 Hz), 3.96 (s, 3H), 3.80 (d, 1H, J=15.0 Hz), 3.68 (d, 1H, J=15.0 Hz), 3.06 (dd, 1H, J=5.5, 11.4 Hz), 2.62 (dd, 1H, J=8.4, 11.3 Hz), 2.45 (s, 3H). HRMS-CI calcd. for C$_{22}$H$_{23}$N$_2$O [M+H]$^+$ 331.1810. Found 331.1829.

Example 21
Preparation of 2-methyl-4-phenyl-7-(3,5-pyrimidyl)-1,2,3,4-tetrahydroisoquinoline Step A: To 5-bromopyrimidine (1.59 g, 10.0 mmol) in anhydrous diethyl ether (125 ml) at −78° C. was added n-BuLi/hexanes (4.25 mmol, 12.5 mmol) over a five minute period. After stirring for 20 minutes at triiosopropyl borate (2.88 ml, 12.5 mmol) was added, and the reaction stirred two hours as the reaction slowly warmed to room temperature. Pinacol (1.60 g, 13.5 mmol) was added, and after ten minutes sufficient acetic acid (0.60 ml, 10.5 mmol) was added to neutralize the solution. The slurry was filtered through celite, and the filter was washed with diethyl ether (5×50 ml). The crude product appeared as a yellow oily solid on the bed of celite and was isolated and recrystallized from hexanes, yielding an amorphous solid (0.40 g): CI MS m/z=207 [M+H]$^+$.

Step B: The product from Example 1, Step B (0.200 g, 0.66 mmol) and the product from Example 21, Step A (206 mg, 1.00 mmol) were combined as described for the synthesis of Example 1, Step C to afford, after chromatography, the product as an oil, (9.2 mg): $^1$H NMR (CDCl$_3$, 300 MHz) δ 9.19 (s, 1H), 8.93 (s, 2H), 7.36-7.21 (m, 7H), 7.03 (m, 1H), 4.34 (t, 1H, J=6.2 Hz), 3.77 (q, 2H), 3.11 (dd, 1H, J=5.8, 11.7 Hz), 2.59 (dd, 1H, J=8.8, 11.3 Hz), 2.48 (s, 3H). HRMS-CI calcd. for C$_{20}$H$_{20}$N$_3$ [M+H]$^+$ 302.1657. Found 302.1664.

Example 22
Preparation of 4-(3,4-difluorophenyl)-2-methyl-7-(3,5-pyrimidyl)-1,2,3,4-tetrahydroisoquinoline The product from Example 18, Step C (0.266 g, 0.79 mmol) in dimethylformamide (4.8 ml) was treated with pinacol diborane (220 mg, 0.87 mmol), potassium acetate (232 mg, 2.37 mmol) and [1,1'-bis(diphenylphosphino)ferrocene] dichloropalladium(II), complex with dichloromethane (1:1) (32 mg, 0.04 mmol). The mixture was heated to 80° C. for two hours under N cooled, treated with 5-bromopyrimidine (251 mg, 1.58 mmol), 2N Na$_2$CO$_3$ (2 ml), and [1,1'-bis(diphenylphosphino)ferrocene] dichloropalladium(II), complex with dichloromethane (1:1) (32 mg, 0.04 mmol). The solution was heated to 80° C. overnight, cooled to room temperature, and extracted with diethyl ether (3×20 ml). The combined organic extracts were washed with water (3×25 ml) and brine (1×25 ml), dried over anhydrous magnesium sulfate, filtered and concentrated in vacuo to yield the product as a red oil. Chromatography (SiO$_2$, 100 g, 5% methanol/ethyl acetate) afforded the product as an oil: (72 mg): $^1$H NMR (CDCl$_3$, 300 MHz) δ 9.19 (s, 1H), 8.83 (s, 2H), 7.29 (m, 2H), 7.14-6.95 (m, 4H), 4.33 (t, 1H, J=6.2 Hz), 3.75 (s, 2H), 3.00 (dd, 1H, J=5.5, 11.7 Hz), 2.63 (dd, 1H, J=7.3, 11.5 Hz), 2.46 (s, 3H). HRMS-CI calcd. for C$_{20}$H$_{18}$N$_3$F$_2$ [M+H]$^+$ 338.1469. Found 338.1470.

Example 23
Preparation of 4-(4-methyl)phenyl-2-methyl-7-(3,5-pyrimidyl)-1,2,3,4-tetrahydroisoquinoline Step A: 3-Bromobenzaldehyde (5,56 g, 3.5 ml, 30.0 mmol) and methylamine (40% aqueous, 3.35 ml, 39 mmol) in methanol (30 ml) was stirred for 10 minutes at room temperature under a nitrogen atmosphere. Sodium borohydride (NaBH$_4$, 0.56 g, 15 mmol) was added portionwise over five minutes and the solution stirred for one hour. Solid 2-bromo-4'-methylacetophenone (6.4 g, 30.0 mmol) was added and the reaction stirred for one hour at room temperature. When the reaction was complete by thin-layer chromatography (3:7 ethyl acetate/hexanes), sodium borohydride (1.13 g, 30.0 mmol) was added and the reaction stirred for twelve hours. The reaction was quenched with water (50 ml) and extracted with methylene chloride (3×40 ml). The combined organic extracts were washed with water (2×40 ml) and dried over anhydrous sodium sulfate, filtered, and concentrated in vacuo. Chromatography (SiO$_2$, 200 g, 3:7 ethyl acetate/hexanes) afforded the product as a viscous yellow liquid (1.89 g): $^1$H NMR (CDCl$_3$, 300 MHz) δ 7.42 (m, 2H), 7.20 (m, 7H), 4.75 (dd, 1H, J=3.6, 10.3 Hz), 3.70 (d, 1H, J=13.0 Hz), 3.50 (d, 1H, J=13.0 Hz), 2.55 (m, 2H), 2.33 (s, 3H), 2.31 (s, 3H).

Step B: The product from Step A (5.52 g, 16.51 mmol) in methylene chloride (650 ml) at 0° C. was treated with 98% sulfuric acid (65 ml) dropwise over 30 minutes. The reaction was stirred for 30 minutes, diluted with water (50 ml) and basified with 25% NH$_4$OH. The product was extracted with methylene chloride (3×50 ml) and the combined organic layers washed with water (2×50 ml), dried over anhydrous magnesium sulfate, filtered and concentrated in vacuo. Chromatography (SiO$_2$, 300 g, 5% methanol/ethyl acetate afforded the product as a viscous light yellow oil (0.50 g): $^1$H NMR (CDCl$_3$, 300 MHz) δ 7.26-7.03 (m, 6H), 6.74 (d, 1H, J=8.4 Hz), 4.15 (m, 1H), 3.71 (d, 1H, J=15.0 Hz), 3.56 (d, 1H, J=15.0 Hz), 3.02 (dd, 1H, J=5.7, 11.5 Hz), 2.51 (dd, 1H, J=9.1, 11.5 Hz), 2.41 (s, 3H,), 2.33 (s, 3H).

Step C: The product from Step B (0.361 g, 0.1.15 mmol) in dimethylformamide (6.9 ml) was treated with pinacol diborane (319 mg, 1.26 mmol), potassium acetate (338 mg, 3.45 mmol) and [1,1'-bis(diphenylphosphino)ferrocene] dichloropalladium(II), complex with dichloromethane (1:1) (47 mg, 0.06 mmol). The reaction was heated to 80° C. for two hours, cooled, and treated with 5-bromopyrimidine (365.6 mg, 2.30 mmol), 2N Na$_2$CO$_3$ (2.9 ml), and [1,1'-bis (diphenylphosphino) ferrocene] dichloropalladium(II), complex with dichloromethane (1:1) (47 mg, 0.06 mmol). This solution was heated to 80° C. overnight, cooled to room temperature and extracted with diethyl ether (3×20 ml). The combined organic extracts were washed with water (3×25 ml) and brine (1×25 ml), dried over anhydrous magnesium sulfate, filtered and concentrated in vacuo to yield the product as a red oil. Chromatography (SiO$_2$, 50 g, 5% methanol/ethyl acetate) afforded the product as an oil: (105 mg): $^1$H NMR (CDCl$_3$, 300 MHz)δ 9.19 (s, 1H), 8.92 (s, 2H), 7.28 (d, 2H), 7.19 (m, 3H), 7.08 (d, 1H, 7.3), 4.29 (t, 1H, J=6.2 Hz), 3.85 (d, 1H, J=15.01 Hz), 3.68 (d, 1H, J=15.0 Hz) 3.07 (dd, 1H, J=5.5, 11.6 Hz), 2.60 (dd, 1H, J=8.8, 11.7 Hz), 2.47 (s, 3H), 2.35 (s, 3H). CI MS m/z=316 [M+H]$^+$. The oil was then converted to its maleate salt by dissolving in a minimal amount of absolute ethanol, adding one equivalent of maleic acid and placing the solution at −30° C. until crystal formation occurred. Filtration yielded a white solid: mp 146.0–147.5° C.

Example 24

Preparation of 2-methyl-4-phenyl-7-(2.6-pyrimidyl)-1,2,3,4-tetrahydroisoquinoline The product from Example 9, Step E (0.50 g, 1.43 mmol) in dimethylformamide (10 ml) was treated with pinacol diborane (400 mg, 1.58 mmol), potassium acetate (420 mg, 4.28 mmol) and [1,1'-bis(diphenylphosphino)ferrocene] dichloropalladium(II), complex with dichloromethane (1:1) (120 mg, 0.15 mmol). The reaction was heated to 80° C., cooled, and treated with 2-bromopyrimidine (453 mg, 2.85 mmol), 2N $Na_2CO_3$ (14.25 ml), and [1,1'-bis(diphenylphosphino)ferrocene] dichloropalladium (II), complex with dichloromethane (1:1) (60 mg, 0.075 mmol). This solution was heated to 80° C. overnight, cooled to room temperature and extracted with diethyl ether (8×20 ml). The combined organic extracts were washed with water (3×25 ml) and brine (1×25 ml), dried over anhydrous magnesium sulfate, filtered and concentrated in vacuo to yield the product as an oil. Chromatography ($SiO_2$, 80 g, 5% methanol/ethyl acetate) afforded the product as an oil (184 mg): $^1$H NMR ($CDCl_3$, 300 MHz) δ 8.79 (d, 2H, J=4.7 Hz), 8.19 (s, 1H), 8.14 (d, 1H, J=8.1 Hz), 7.25 (m, 6H), 7.01 (d, 1H, J=8.0 Hz), 4.35 (t, 1H, J=7.2 Hz), 3.88 (d, 1H, J=14.8 Hz), 3.72 (d, 1H, J=14.8 Hz), 3.09 (dd, 1H, J=5.7, 11.6 Hz), 2.61 (dd, 1H, J=8.8, 11.4 Hz), 2.47 (s, 3H). HRMS-CI calcd. for $C_{20}H_{20}N_3$ [M+H]$^+$ 302.1657. Found 302.1655.

Example 25

Preparation of 7-(2.5-dimethyl-4-isoxazole)-4-(4-methoxy)phenyl-2-methyl-1,2,3,4-tetrahydroisoquinoline Example 25 was prepared by the method exemplified in Example 1, step C.

Step A: To 4-methoxyacetophenone (10.0 g, 66.6 mmol) in acetic acid (100 ml) was added bromine (3.43 ml, 66.6 mmol). The resulting solution was stirred at room temperature for 48 hours. Concentration in vacuo afforded an orange liquid which was made basic with saturated $NaHCO_3$ and the layers separated. The organic layer was washed with water (2×50 ml) and brine (1×50 ml), dried over anhydrous magnesium sulfate and evaporated to a red oil (15.34 g). Chromatography ($SiO_2$, 500 g, 3:7 ethyl acetate/hexanes) afforded the product as a red oil (4.66 g): $^1$H NMR ($CDCl_3$, 300 MHz)·7.97 (d, 2H, J=8.8 Hz), 6.96 (d, 2H, J=8.8 Hz), 4.4 (s, 2H), 3.90 (s, 3H).

Step B: A solution of 3-bromobenzaldehyde (3.76 g, 2.4 ml, 20.3 mmol) and methylamine (40% aqueous, 7.3 ml, 26.6 mmol) in methanol (22 ml) was stirred for 10 minutes at room temperature. Sodium borohydride (385 mg, 10.17 mmol) was added portionwise over five minutes and the solution stirred for one hour. The product from Step A (15.4 g, 65.0 mmol) was added to the reaction mixture and the reaction stirred for one hour. When the reaction was complete by thin-layer chromotography (3:7 ethyl acetate/hexanes), a full equivalent of sodium borohydride (769 mg, 20.3 mmol) was slowly added and the reaction stirred for one hour. The reaction was quenched with water (50 ml) and the solution was extracted with methylene chloride (3×40 ml). The combined organic extracts were washed with water (2×40 ml), dried over anhydrous sodium sulfate, filtered, and concentrated in vacuo. Chromatography ($SiO_2$, 500 g, 3:7 ethyl acetate/hexanes) afforded the product as a viscous yellow oil, (3.51 g): $^1$H NMR ($CDCl_3$, 300 MHz)·7.47-7.40 (m, 2H), 7.30-7.20 (m, 4H), 6.88 (d, 2H, J=8.0 Hz), 4.71 (dd, 1H, J=4.2, 10.8 Hz), 3.80 (s, 3H), 3.69 (d, 1H, J=13.4 Hz), 3.50 (d, 1H, J=13.4 Hz), 2.60-2.46 (m, 2H), 2.31 (s, 3H).

Step C: The product from Step B (4.55 g, 11.6 mmol) in dichloroethane (34 ml) was added dropwise to methanesulfonic acid (53 ml) at 40° C. over 5 minutes. The reaction was stirred at for 30 minutes at 40° C. and then 60 minutes at 80° C. until thin-layer chromatography (1:1 ethyl acetate/hexanes) indicated the reaction was complete. The reaction was poured onto ice (300 ml) and the solution slowly basified with $NH_4OH$ (conc). The product was extracted with ethyl acetate (5×100 ml) and the combined organic layers washed with water (2×50 ml), dried over anhydrous magnesium sulfate, filtered and concentrated in vacuo. Chromatography ($SiO_2$, 250 g, 1:1 ethyl acetate/hexanes) afforded the product as a viscous light yellow oil (2.62 g): $^1$H NMR ($CDCl_3$, 300 MHz).7.22 (t, 2H, J=8.5 Hz), 7.08 (d, 2H, J=8.8 Hz), 6.83 (d, 2H, J=8.8 Hz), 6.75 (d, 1H, J=8.5 Hz), 4.18-4.11 (m, 1H), 3.79 (s, 3H), 3.71 (s, 3H), 3.71 (d, 1H, J=15.20 Hz), 3.56 (d, 1H, J=15.20 Hz), 2.98 (q, 1H, J=4.4, 11.7 Hz), 2.50 (t, 1H, J=10.0 Hz), 2.42 (s, 3H).

Step D: The product from Example 25, Step C (0.5 g, 1.5 mmol) and 3,5-dimethylisoxazole-4-boronic acid (317 mg, 2.25 mmol) afforded, after chromatography, the product as a yellow oil which was further purified by reverse phase high pressure liquid chromatography on a C18 column using acetonitrile/water as eluent (165 mg): $^1$H NMR ($CDCl_3$, 300 MHz). 7.15 (d, 2H, J=8.8 Hz), 6.95 (s, 3H), 6.86 (d, 2H, J=8.8 Hz), 4.24 (m, 1H), 3.81 (s, 3H), 2.79 (d, 1H, J=14.6 Hz), 3.62 (d, 1H, J=15 Hz), 3.02 (q, 1H, J=5.5, 11.4 Hz), 2.56 (t, 1H, J=10.1 Hz), 2.45 (s, 3H), 2.39 (s, 3H), 2.25 (s, 3H). HRMS-CI calcd. for $C_{22}H_{25}N_2O_2$ [M+H]$^+$ 349.1917. Found 349.1918.

Example 26

Preparation of 4-(4-methoxy)phenyl-2-methyl-7-(2-pyridyl)-1,2,3,4-tetrahydroisoquinoline Example 26 was prepared by the method exemplified in Example 15.

The product from Example 25, Step C (0.5 g, 1.5 mmol) and 2-bromopyridine (474 mg, 3 mmol) afforded, after chromatography, the product as a yellow oil which was further purified by reverse phase high pressure liquid chromatography on a C18 column using acetonitrile/water as eluent (66 mg): $^1$H NMR ($CDCl_3$, 300 MHz). 8.67 (d, 1H, J=5 Hz), 7.76-7.63 (m, 4H), 7.23-7.20 (m, 1H), 7.12 (d, 2H, J=8.8 Hz), 6.99 (d, 1H, J=8 Hz), 6.85 (d, 2H, J=8.8 Hz), 4.27 (m, 1H), 3.86 (d, 1H, J=15.2 Hz), 3.80 (s, 3H), 3.68 (d, 1H, J=15.2 Hz), 3.04 (q, 1H, J=5.8, 11.55 Hz), 2.55 (t, 1H, J=10.1 Hz), 2.45 (s, 3H). HRMS-CI calcd. for $C_{22}H_{23}N_2O$ [M+H]$^+$ 331.1811. Found 331.1832.

Binding Assays

Primary Binding Assays:

In order to evaluate the relative affinity of the various compounds at the NE, DA and 5HT transporters, HEK293E cell lines were developed to express each of the three human transporters. cDNAs containing the complete coding regions of each transporter were amplified by PCR from human brain libraries. The cDNAs contained in pCRII vectors were sequenced to verify their identity and then subcloned into an Epstein-Barr virus based expression plasmid (E. Shen, GM Cooke, RA Horlick, Gene 156:235–239, 1995). This plasmid containing the coding sequence for one of the human transporters was transfected into HEK93E cells. Successfil transfection was verified by the ability of known reuptake blockers to inhibit the uptake of tritiated NE, DA or 5HT.

For binding, cells were homogenized, centrifuged and then resuspended in incubation buffer (5 mM Tris, 120 mM NaCl, 5 mM KCl, pH 7.4). Then the appropriate radioligand was added. For NET binding, [$^3$H] Nisoxetine (86.0 Ci/mmol, NEN/DuPont) was added to a final concentration of approximately 5 nM. For DAT binding, [$^3$H] WIN 35,428 (84.5 Ci/mmol) at 15 nM was added. For 5HTT binding, [$^3$H] Citolapram (85.0 Ci/mmol) at 1 nM was added. Then various concentrations (10^-5 to 10^-11 M) of the compound of interest were added to displace the radioligand. Incubation was carried out at room temperature for 1 hour in a 96 well plate. Following incubation, the plates were placed on a harvester and washed quickly 4 times with (50 mM tris, 0.9% NaCl, pH 7.4) where the cell membranes containing the bound radioactive label were trapped on Whatman GF/B filters. Scintillation cocktail was added to the filters which were then counted in a Packard TopCount. Binding affinities of the compounds of interest were determined by non-linear curve regression using GraphPad Prism 2.01 software. Non-specific binding was determined by displacement with 10 micromolar mazindol.

TBZ Assay

In order to assess in vivo activity of the compounds at the NE and DA transporters, their ability to prevent the sedative effects of tetrabenazine (TBZ) was determined (G. Stille, Arzn. Forsch 14:534–537, 1964). Male CFI mice (Charles River Breeding Laboratories) weighing 18–25 gm at the time of testing, are housed a minimum of 06 days under carefully controlled environmental conditions (22.2+1.1 C; 50% average humidity, 12 hr lighting cycle/24 hr). Mice are fasted overnight (16–22 hr) prior to testing. Mice are placed into clear polycarbonated "shoe" boxes (17 cm×28.5 cm×12 cm). Randomized and coded doses of test compounds are administered p.o. A 45 mg/kg dose of tetrabenazine is administered i.p. 30 minutes prior to score time. All compounds are administered in a volume of 0.1 ml/10 gm body weight. Animals are evaluated for antagonism of tetrabenazine induced exploratory loss and ptosis at specified time intervals after drug administration. At the designated time interval, mice are examined for signs of exploratory activity and ptosis. Exploratory activity is evaluated by placing the animal in the center of a 5 inch circle. Fifteen seconds are allowed for the animal to move and intersect the perimeter. This is considered antagonism of tetrabenazine and given a score of 0. Failure to leave the circle is regarded as exploratory loss and given a score of 4. An animal is considered to have ptosis if its eyelids are at least 50% closed and given a score of 4 if completely closed; no closure is given a score of 0. Greater than 95% of the control (vehicle-treated) mice are expected to exhibit exploratory loss and ptosis. Drug activity is calculated as the percentage of mice failing to respond to the tetrabenazine challenge dose.

Statistical Evaluation

Median effective doses (ED$_{50}$s) and 95% confidence limits are determined numerically by the methods of Thompson (1947) and Litchfield and Wilcoxon (1949).

What is claimed is:
1. A compound of the formula (I):

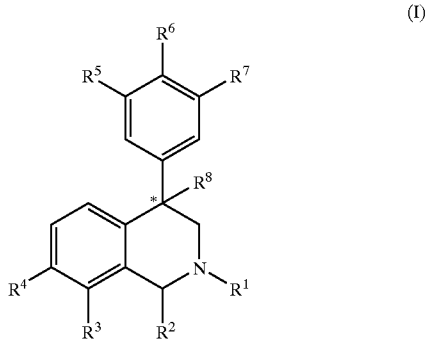

wherein:
the carbon atom designated * is in the R or S configuration;
$R^1$ is $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, each of which is optionally substituted with from 1 to 3 substituents independently selected at each occurrence thereof from the group: $C_1$–$C_3$ alkyl, halogen, Ar, —CN, —OR$^9$ and —NR$^9$R$^{10}$;
$R^2$ is H, $C_1$—$C_6$ alkyl, $C_2$–$C_6$ alkenyl, $C_2$–$C_6$ alkynyl, $C_3$–$C_6$ cycloalkyl, $C_4$–$C_7$ cycloalkylalkyl or $C_1$–$C_6$ haloalkyl;
$R^3$ is H, halogen, —OR$^{11}$, —S(O)$_n$R$^{12}$, —CN, —C(O)R$^{12}$, —C(O)NR$^{11}$R$^{12}$, $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl and wherein each of $C_1$—$C_6$ alkyl, $C_2$–$C_6$ alkenyl, $C_2$–$C_6$ alkynyl, $C_3$–$C_6$ cycloalkyl and $C_4$–$C_7$ cycloalkylalkyl is optionally substituted with from 1 to 3 substituents independently selected at each occurrence thereof from the group: $C_1$–$C_3$ alkyl, halogen, —CN, —OR$^9$, and —NR$^9$R$^{10}$ and phenyl which is optionally substituted 1–3 times with a sub stituent selected from the group: halogen, cyano, $C_1$–$C_4$ alkyl, $C_1$–$C_4$ haloalkyl, or $C_1$–$C_4$ alkoxy, —CN, —OR$^9$, and
$R^4$ is phenyl, naphthyl, indenyl, pyridyl, pyrimidinyl, triazinyl, triazolyl, furanyl, pyranyl, indazolyl, benzimidazolyl, quinolinyl, quinazolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl or thiadiazolyl, wherein the $R^4$ group is optionally substituted with from 1 to 4 $R^{14}$ substituents;
$R^5$ and $R^6$ and $R^7$ are each independently selected from the group: H, halogen, —OR$^{11}$, —NR$^{11}$N$^{12}$, —NR$^{11}$C(O)R$^{12}$, —NR$^{11}$C(O)$_2$R$^{12}$, —NR$^{11}$C(O)NR$^{12}$R$^{13}$, —S(O)$_n$R$^{12}$, —CN, —C(O)R$^{12}$, —C(O)NR$^{11}$R$^{12}$, $C_1$–$C_6$ alkyl, $C_2$–$C_6$ alkenyl, $C_2$–$C_6$ alkynyl, $C_3$–$C_6$ cycloalkyl or $C_4$–$C_7$ cycloalkylalkyl, and wherein each of $C_1$–$C_6$ alkyl, $C_2$–$C_6$ alkenyl, $C_2$–$C_6$ alkynyl, $C_3$–$C_6$ cycloalkyl and $C_4$–$C_7$ cycloalkylalkyl is optionally substituted with from 1 to 3 substituents independently selected at each occurrence thereof from the group: $C_1$–$C_3$ alkyl, halogen, —CN, —OR$^9$, —NR$^9$R$^{10}$ and phenyl which is optionally substituted 1–3 times with a substituent selected from the group: halogen, cyano, $C_1$–$C_4$ alkyl, $C_1$–$C_4$ haloalkyl, or $C_1$–$C_4$ alkoxy, —CN, —OR$^9$, —NR$^9$R$^{10}$;
or $R^5$ and $R^6$ taken together may be —O—C(R$^{12}$)$_2$—O—;

$R^8$ is H, halogen or $OR^{11}$;

$R^9$ and $R^{10}$ are each independently selected from the group H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, —$C(O)R^{13}$, phenyl and benzyl, where phenyl or benzyl is optionally substituted from 1 to 3 times with a substituent selected independently at each occurrence thereof from the group: halogen, cyano, $C_1$–$C_4$ alkyl, $C_1$–$C_4$ haloalkyl and $C_1$–$C_4$ alkoxy;

or $R^9$ and $R^{10}$ are taken together with the nitrogen to which they are attached to form a piperidine, pyrrolidine, piperazine, N-methylpiperazine, morpholine or thiomorpholine ring;

$R^{11}$ is H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, —$C(O)R_{13}$, phenyl or benzyl, where phenyl or benzyl is optionally substituted 1 to 3 times with halogen, cyano, $C_1$–$C_4$ alkyl, $C_1$–$C_4$ haloalkyl, or $C_1$–$C_4$ alkoxy;

$R^{12}$ is H, $C_1$–$C_4$ alkyl, $C_1$–$C_4$ haloalkyl, $C_1$–$C_4$ alkoxyalkyl, $C_3$–$C_6$ cycloalkyl, $C_4$–$C_7$ cycloalkylalkyl, phenyl or benzyl, where phenyl or benzyl is optionally substituted 1 to 3 times with halogen, cyano, $C_1$–$C_4$ alkyl, $C_1$–$C_4$ haloalkyl, or $C_1$–$C_4$ alkoxy;

or $R^{11}$ and $R^{12}$ are taken together with the nitrogen to which they are attached to form a piperidine, pyrrolidine, piperazine, N-methylpiperazine, morpholine or thiomorpholine ring, with the proviso that only one of $R^9$ and $R^{10}$ or $R^{11}$ and $R^{12}$ are taken together with the nitrogen to which they are attached to form a piperidine, pyrrolidine, piperazine, N-methylpiperazine, morpholine or thiomorpholine ring;

$R^{13}$ is $C_1$–$C_4$ alkyl, $C_1$–$C_4$ haloalkyl or phenyl;

n is 0, 1, or 2; and, $R^{14}$ is independently selected at each occurrence from a substituent selected from the group: halogen, —$NO_2$, —$OR^{11}$, —$NR^{11}R^{12}$, —$NR^{11}C(O)R^{12}$, —$NR^{11}C(O)_2R^{12}$, —$NR^{11}C(O)NR^{12}R^{13}$, —$S(O)_nR^{12}$, —CN, —$C(O)R^{12}$, —$C(O)NR^{11}R^{12}$, $C_1$–$C_6$ alkyl, $C_2$–$C_6$ alkenyl, $C_2$–$C_6$ alkynyl, $C_3$–$C_6$ cycloalkyl, and $C_4$–$C_7$ cycloalkylalkyl, where $C_1$–$C_6$ alkyl, $C_2$–$C_6$ alkenyl, $C_2$–$C_6$ alkynyl, $C_3$–$C_6$ cycloalkyl, $C_4$–$C_7$ cycloalkylalkyl are optionally substituted with 1 to 3 substituents independently selected at each occurrence from the group consisting of $C_1$–$C_3$ alkyl, halogen, Ar, —CN, —$OR^9$, and —$NR^9R^{10}$, or an oxide thereof, or a pharmaceutically acceptable salt thereof.

2. The compound of claim 1, wherein $R^1$ is $C_1$–$C_6$ alkyl.

3. The compound of claim 2, wherein $R^1$ is methyl.

4. The compound of claim 1, wherein $R^2$ is H, $C_1$–$C_6$ alkyl or $C_1$–$C_6$ haloalkyl.

5. The compound of claim 4, wherein $R^2$ is H or $C_1$–$C_6$ alkyl.

6. The compound of claim 5, wherein $R^2$ is H.

7. The compound of claim 1, wherein $R^3$ is H, halogen, —$OR^{11}$, —$S(O)_2R^{12}$, $C_1$–$C_6$ alkyl or substituted $C_1$–$C_6$ alkyl.

8. The compound of claim 7, wherein $R^3$ is H.

9. The compound of claim 1, wherein $R^4$ is phenyl optionally and independently substituted from 1 to 4 times with $R^{14}$.

10. The compound of claim 9, wherein the $R^4$ is phenyl, 2-chlorophenyl, 3-chlorophenyl, 4-chlorophenyl, 2-methoxyphenyl, 3-methoxyphenyl, 4-methoxyphenyl or 4-dimethylaminophenyl.

11. The compound of claim 1, wherein $R^4$ is pyridyl, pyrimidinyl, triazinyl, triazolyl, furanyl, pyranyl, indazolyl, benzimidazolyl, quinolinyl, quinazolinyl, isoquinolinyl, thienyl, imidazolyl, thiazolyl, benzthiazolyl, purinyl, isothiazolyl, indolyl, pyrrolyl, oxazolyl, benzofuranyl, benzothienyl, benzthiazolyl, isoxazolyl, pyrazolyl, oxadiazolyl, or thiadiazolyl, which is optionally substituted 1–4 times with $R^{14}$.

12. The compound of claim 11, wherein $R^4$ is 4-methyl-2-furanyl, 5-methyl-2-furanyl, 3-furanyl, 2-thienyl, 3-thienyl, 3,5-dimethyl-4-isoxazolyl, 2-pyridyl, 3-pyridyl, 4-pyridyl, 2-methoxy-3-pyridyl, 6-methoxy-3-pyridyl, 3,5-pyrimidinyl or 2,6-pyrimidinyl.

13. The compound of claim 1, wherein $R^5$, $R^6$ and $R^7$ are each independently selected from the group: H, halogen, —$OR^{11}$, —$NR^{11}R^{12}$, —, —$S(O)_2R^{12}$, —$C(O)R^{12}$, and optionally substituted $C_1$–$C_6$ alkyl.

14. The compound of claim 13, wherein $R^7$ is H.

15. The compound of claim 14, wherein of $R^5$ and $R^6$ are each H, F, Cl, OH, $OCH_3$ or $CH_3$.

16. The compound of claim 1, wherein $R^8$ is H, OH, or F.

17. The compound of claim 1, wherein $R^1$ is $C_1$–$C_6$ alkyl;

$R^2$ is H, $C_1$–$C_6$ alkyl or $C_1$–$C_6$ haloalkyl;

$R^3$ is H, halogen, —$OR^{11}$, —$S(O)_2R^{12}$, $C_1$–$C_6$ alkyl or substituted $C_1$–$C_6$ alkyl;

$R^4$ is aryl or heteroaryl; and $R^5$, $R^6$ and $R^7$ are each independently selected from the group: H, halogen, —$OR^{11}$, —$NR^{11}R^{12}$, —$S(O)_2R^{12}$, —$C(O)R^{12}$, $C_1$–$C_6$ alkyl and substituted $C_1$–$C_6$ alkyl.

18. The compound of claim 1, wherein $R^1$ is methyl;

$R^2$ is H;

$R^3$ is H;

$R^5$ and $R^6$ are each independently selected from the group: H, F, Cl, OH, $OCH_3$, and $CH_3$;

$R^7$ is H or F;

$R^8$ is H, OH, or F; and $R^4$ is phenyl, pyridyl, pyrimidinyl, triazinyl, triazolyl, furanyl, pyranyl, indazolyl, thienyl, imidazolyl, thiazolyl, purinyl, isothiazolyl, indolyl, pyrrolyl, oxazolyl, isoxazolyl, or pyrazolyl, each of which $R^4$ is optionally and independently substituted from 1–4 times with $R^{14}$.

19. The compound of claim 1, wherein $R^1$ is methyl;

$R^2$ is H;

$R^3$ is H;

$R^5$ and $R^6$ are each H, F or $CH_3$;

$R^7$ is H;

$R^8$ is H; and $R^4$ is phenyl, 2-chlorophenyl, 3-chlorophenyl, 4-chlorophenyl, 2-methoxyphenyl, 3-methoxyphenyl, 4-methoxyphenyl, 4-dimethylaminophenyl, 4-methyl-2-furanyl, 5-methyl-2-furanyl and 3-furanyl, 2-thienyl and 3-thienyl, 3,5-dimethyl-4-isoxazolyl, 2-pyridyl, 3-pyridyl, 4-pyridyl, 2-methoxy-3-pyridyl and 6-methoxy-3-pyridyl 3,5-pyrimidinyl or 2,6-pyrimidinyl.

20. A compound according to claim 1, wherein the carbon atom designated * is in the R configuration.

21. A compound according to claim 1, wherein the carbon atom designated * is in the S configuration.

22. A compound according to claim 1, selected from the group:

4,7-diphenyl-2-methyl-1,2,3,4-tetrahydroisoquinoline;

7-(2-chloro)phenyl-2-methyl-4-phenyl-1,2,3,4-tetrahydroisoquinoline;

7-(3-chloro)phenyl-2-methyl-4-phenyl-1,2,3,4-tetrahydroisoquinoline;
7-(4-chloro)phenyl-2-methyl-4-phenyl-1,2,3,4-tetrahydroisoquinoline;
7-(2-methoxy)phenyl-2-methyl-4-phenyl-1,2,3,4-tetrahydroisoquinoline;
7-(3-methoxy)phenyl-2-methyl-4-phenyl-1,2,3,4-tetrahydroisoquinoline;
7-(4-methoxy)phenyl-2-methyl-4-phenyl-1,2,3,4-tetrahydroisoquinoline;
7-(4-N,N-dimethylamino)phenyl-2-methyl-4-phenyl-1,2,3,4-tetrahydroisoquinoline;
7-[(4-methyl)-2-thienyl]-2-methyl-4-phenyl-1,2,3,4-tetrahydroisoquinoline;
7-[(5-methyl)-2-furanyl]-2-methyl-4-phenyl-1,2,3,4-tetrahydroisoquinoline;
7-(3-furanyl)-2-methyl-4-phenyl-1,2,3,4-tetrahydroisoquinoline;
2-methyl-4-phenyl-7-(2-thienyl)-1,2,3,4-tetrahydroisoquinoline;
2-methyl-4-phenyl-7-(3-thienyl)-1,2,3,4-tetrahydroisoquinoline;
7-[(3,5-dimethyl)-4-isoxazole]-2-methyl-4-phenyl-1,2,3,4-tetrahydroisoquinoline;
2-methyl-4-phenyl-7-(2-pyridyl)-1,2,3,4-tetrahydroisoquinoline;
2-methyl-4-phenyl-7-(3-pyridyl)-1,2,3,4-tetrahydroisoquinoline;
2-methyl-4-phenyl-7-(4-pyridyl)-1,2,3,4-tetrahydroisoquinoline;
4-(3,4-difluoro)phenyl-2-methyl-7-(3-pyridyl)-1,2,3,4-tetrahydroisoquinoline;
7-[(2-methoxy)-3-pyridyl]-2-methyl-4-phenyl-1,2,3,4-tetrahydroisoquinoline;
7-[(6-methoxy)-3-pyridyl]-2-methyl-4-phenyl-1,2,3,4-tetrahydroisoquinoline;
2-methyl-4-phenyl-7-(3,5-pyrimidyl)- 1,2,3,4-tetrahydroisoquinoline;
4-(3,4-difluoro)phenyl-2-methyl-7-(3,5-pyrimidyl)-1,2,3,4-tetrahydroisoquinoline;
4-(4-methyl)phenyl-2-methyl-7-(3,5-pyrimidyl)-1,2,3,4-tetrahydroisoquinoline;
2-methyl-4-phenyl-7-(2,6-pyrimidyl)-1,2,3,4-tetrahydroisoquinoline;
7-(2,5-dimethyl-4-isoxazole)-4-(4-methoxy)phenyl-2-methyl-1,2,3,4-tetrahydroisoquinoline; and
4-(4-methoxy)phenyl-2-methyl-7-(2-pyridyl)-1,2,3,4-tetrahydroisoquinoline or an oxide thereof, or a pharmaceutically acceptable salt thereof.

23. A compound according to claim 22, which is the (+) stereoisomer.

24. A compound according to claim 22, which is the (−) stereoisomer.

25. A pharmaceutical composition comprising a pharmaceutically acceptable carrier and a therapeutically effective amount of the compound of claim 1.

* * * * *